(12) United States Patent
Dubin et al.

(10) Patent No.: US 7,109,296 B2
(45) Date of Patent: Sep. 19, 2006

(54) HUMAN 5-HT3-C PROTEIN

(75) Inventors: Adrienne E. Dubin, San Diego, CA (US); Mark G. Erlander, Encinitas, CA (US); Arne Huvar, Bmo-Komin (CZ); Rene Huvar, Bmo-Komin (CZ); Lukas K. Buehler, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 395 days.

(21) Appl. No.: 10/661,378

(22) Filed: Sep. 12, 2003

(65) Prior Publication Data

US 2005/0124795 A1  Jun. 9, 2005

Related U.S. Application Data

(60) Continuation of application No. 09/955,524, filed on Sep. 12, 2001, now abandoned, which is a division of application No. 09/388,349, filed on Sep. 1, 1999, now Pat. No. 6,365,370.

(51) Int. Cl.
*C07K 14/705* (2006.01)

(52) U.S. Cl. ...................................... 530/350

(58) Field of Classification Search ...................... None
See application file for complete search history.

(56) References Cited

U.S. PATENT DOCUMENTS 6,462,188 B1 * 10/2002 Kirkness ..................... 536/23.5

FOREIGN PATENT DOCUMENTS

| WO | WO 0071741 | 11/2000 |
|---|---|---|
| WO | WO 0202639 | 1/2002 |

OTHER PUBLICATIONS

Bruss M. et al. Molecular cloning of alternatively spliced human 5-HT3 receptor cDNAs, Ann. N.Y. Acad. Sci. 861: 234-235 (1998).*
Barnard, "The Transmitter-Gated Channels: A Range Of Receptor Types And Structures," *Trends Pharmacol. Sci.*, vol. 17, pp. 305-309 (1996).
Belelli et al., "Cloning And Functional Expression Of A Human 5-Hydroxytryptamine Type-3$A_s$ Receptor Subunit," *Mol. Pharmacol.*, vol. 48, pp. 1054-1062 (1995).
Boess et al., "Analysis Of The Ligand Binding Site Of The 5-HT$_3$ Receptor Using Site Directed Mutagenesis: Importance Of Glutamate 106," *Neuropharm.*, vol. 36, pp. 637-647 (1997).
Bufton et al., "Distribution And Characterization Of The [$^3$H]Granisetron-Labelled 5-HT$_3$ Receptor In The Human Forebrain," *Neuropharm.*, vol. 32(12), pp. 1325-1331 (1993).
Davies et al., "The 5-HT$_{3-B}$ Subunit Is A Major Determinant Of Serotonin-Receptor Function", *Nature (London)*, vol. 397, pp. 359-363 (1999).
Derkach et al., "5-HT$_3$ Receptors Are Membrane Ion Channels," *Nature (London)*, vol. 339, pp. 706-709 (1989).
Fletcher et al., "Desperately Seeking Subunits: Are Native 5-HT$_3$ Receptors Really Homomeric Complexes?" *Trends Pharmacol. Sci.*, vol. 19, pp. 212-215 (1998).
Fletcher et al., "Purification Of 5-Hydroxytryptamine-$_3$ Receptors From Porcine Brain", *Br. J. Pharmacol.*, vol. 122, pp. 655-662 (1997).
Fletcher et al., "Evidence That Porcine Native 5-HT$_3$ Receptors Do Not Contain Nicotinic Acetylcholine Receptor Subunits", *Neuropharm.*, vol. 37, pp. 397-399 (1998).
Furutani et al., "Novel Mechanism Associated With An Inherited Cardiac Arrhythmia: Defective Protein Trafficking By The Mutant HERG (G601S) Potassium Channel", *Circulation*, vol. 99, pp. 2290-2294 (1999).
Gralla, "Antiemetic Therapy,"*Semin. Oncol.*, vol. 25, pp. 577-583 (1998).
Greenshaw et al., "The Non-Antiemetic Uses Of Serotonin 5-HT$_3$ Receptor Antagonists: Clinical Pharmacology and Therapeutic Applications," *Drugs*, vol. 53(1), pp. 20-39 (1997).
Gurley et al., "Nicotinic Agonists Competitively Antagonize Serotonin At Mouse 5-HT$_3$ Receptors Expressed In Xenopus Oocytes," *Neurosci. Letters*, vol. 247, pp. 107-110 (1998).
Hugnot et al., "Kv8.1, A New Neuronal Potassium Channel Subunit with Specific Inhibitory Properties Towards *Shab* And *Shaw* Channels," *EMBO J.*, vol. 15(13), pp. 3322-3331 (1996).
Jan et al., "Voltage-Gated And Inwardly Rectifying Potassium Channels," *J. Physiology*, vol. 505(2), pp. 267-282 (1997).
Lambert et al., "5-HT3 Receptors" In *Ligand- Voltage-Gated Ion Channels*, (R. North (Ed.), CRC Press—Boca Raton, Fl), Chp. 5, pp. 177-211 (1995).
Lummis et al., "Radioligand Binding And Photoaffinity Labeling Studies Show A Direct Interaction Of Phenothiazines At 5-HT$_3$ Receptors," *Neuropharm.*, vol. 36(4/5), pp. 665-670 (1997).
Lummis et al., "Solubilization, Purification, And Functional Reconstitution Of 5-Hydroxytryptamine$_3$ Receptors From N1E-115 Neuroblastoma Cells," *Mol. Pharmacol.*, vol. 41, pp. 18-23 (1992).
Lummis et al., "Characterization Of [$^3$H]Metachlorophenylbiguanide Binding To 5-HT$_3$ Receptors In N1E-115 Neuroblastoma Cells," *Eur. J. Pharmacol.*, vol. 243, pp. 7-11 (1993).
Maricq et al., "Primary Structure And Functional Expression Of The 5HT$_3$ Receptor: A Serotonin-Gated Ion Channel," *Science (Washington, D. C.)*, vol. 254, pp. 432-437 (1991).
Mathur et al., "Ile-177 And Ser-180 In The S1 Segment Are Critically Important In Kv1.1 Channel Function," *J. Biol. Chem.*, vol. 274(17), pp. 11487-11493 (1999).

(Continued)

*Primary Examiner*—Janet L. Andres
*Assistant Examiner*—Kimberly A. Ballard

(57) ABSTRACT

DNA encoding human 5-HT3-C has been cloned and characterized. The recombinant protein is capable of forming biologically active human 5-HT3-C protein. The cDNA has been expressed in recombinant host cells that produce active recombinant protein. In addition, the recombinant host cells are utilized to establish a method for identifying modulators of the receptor activity, and receptor modulators are identified.

2 Claims, 8 Drawing Sheets

OTHER PUBLICATIONS

Mikayama et al., "Molecular Cloning And Functional Expression Of A cDNA Encoding Glycosylation-Inhibiting Factor," *Proc. Natl. Acad. Sci. USA*, vol. 90, pp. 10056-10060 (1993).

Miller et al., "Membrane-Bound And Solubilized Brain $5HT_3$ Receptors: Improved Radioligand Binding Assays Using Bovine Area Postrema Or Rat Cortex And The Radioligands $^3$H-GR65630, $^3$H-BRL43694, And $^3$H-LY278584," *Synapse (NY)*, vol. 11, pp. 58-66 (1992).

Miyake et al., "Molecular Cloning of Human 5-Hydroxytryptamine$_3$ Receptor: Heterogeneity In Distribution And Function Among Species," *Mol. Pharmacol.*, vol. 48, pp. 407-416 (1995).

Passani et al., "Therapeutic Potentials of Itasetron (DAU 6215), A Novel $5-HT_3$ Receptor Antagonist, In The Treatment Of Central Nervous System Disorders," *CNS Drug Rev.*, vol. 2, pp. 195-213 (1996).

Peters et al., "Recent Advances in the Electrophysiological Characterization of $5-HT_3$ Receptors," *Trends Pharmacol. Sci.*, vol. 13, pp. 391-397 (1992).

Salinas et al., "Modes of Regulation Of *Shab* K$^+$Channel Activity By The Kv8.1 Subunit," *J. Biol. Chem.*, vol. 272(13), pp. 8774-8780 (1997).

Salinas et al., "New Modulatory α Subunits For Mammalian *Shab* K$^+$Channels," *J. Biol. Chem.*, vol. 272(39), pp. 24371-24379 (1997).

Shalaby et al., "Dominant-Negative *KvLQT1* Mutations Underlie The LQT1 Form Of Long QT Syndrome," *Circulation*, vol. 96(6), pp. 1733-1736 (1997).

Shuck et al., "Cloning And Characterization Of Two K$^+$Inward Rectifier ($K_{ir}$) 1.1 Potassium Channel Homologs From Human Kidney ($K_{ir}$1.2 and $K_{ir}$1.3)," *J. Biological Chem.*, vol. 272(1), pp. 586-593 (1997).

Steward et al., "Labeling of $5-HT_3$ Receptor Recognition Sites In The Rat Brain Using The Agonist Radioligand [3H]Metachlorophenylbiguanide," *Eur. J. Pharmacol.*, vol. 243, pp. 13-18 (1993).

Stocker et al., "Subunit Assembly And Domain Analysis Of Electrically Silent K$^+$Channel (alpha)-Subunits Of The Rat Kv9 Subfamily," *J. Neurochem.*, vol. 72(4), pp. 1725-1734 (1999).

Sugita et al., "5-Hydroxytryptamine Is A Fast Excitatory Transmitter At $5-HT_3$ Receptors In Rat Amygdala," *Neuron*, vol. 8, pp. 199-203 (1992).

Turton et al., "Antibodies Against The $5-HT_3$-A Receptor Identify A 54 kDa Protein Affinity-Purified From NCB20 Cells," *Mol. Neuropharmacol.*, vol. 3, pp. 167-171 (1993).

Van Hooft et al., "Phosphorylation Controls Conductance of $5-HT_3$ Receptor Ligand-Gated Ion Channels," *Recept. Channels*, vol. 3, pp. 7-12 (1995).

Voet et al., "Biochemistry," John Wiley & Sons, Inc., pp. 126-129 and pp. 228-234 (1990).

Waeber et al., "5-HT3 Receptors In The Human Brain: Autoradiographic Visualization Using [$^3$H]ICS 205-930," *Neuroscience*, vol. 31(2), pp. 393-400 (1989).

Yakel et al., "Activation And Desensitization Of The $5-HT_3$ Receptor In A Rat Glioma x Mouse Neuroblastoma Hybrid Cell," *J. Physiol. (London)* vol. 436, pp. 293-308 (1991).

Zerr et al., "Episodic Ataxia Mutations in Kv1.1 Alter Potassium Channel Function By Dominant Negative Effects Or Haploinsufficiency," *J. Neuroscience*, vol. 18(8), pp. 2842-2848 (1998).

Dubin et al., "The Pharmacological And Functional Characteristics Of The Serotonin $5-HT_{3A}$ Receptor Are Specifically Modified By A $5-HT_{3B}$ Receptor Subunit," *J. Bio. Chem.*, vol. 274(43), pp. 30799-30810 (1999).

Miquel et al., "Developmental Changes In the Differential Expression Of Two Serotonin $5-HT_3$ Receptor Splice Variants In The Rat," *J. Neurochemistry*, vol. 65(2), pp. 475-483 (1995).

* cited by examiner

FIGURE 1

[SEQ.ID.NO.:5] Nucleic Acid sequence of the human 5-HT3-C (full sequence including untranslated regions); 1745 bases. ( 34 bases of 5' UTR; 367 bases of 3' UTR)

TGGTGAATCCCCAGAGAAGAGTCCAGAAAGAAGAATGGAAGGAGGGTGGCCTGCAAGGCAGAGTGCCCT
CCTCTGCCTCACTGTCAGTCTTCTGCTTCAAGGAAGAGGCGACGCTTTTACCATCAATTGCTCAGGCTT
TGACCAGCATGGGGTTGACCCTGCTGTCTTCCAAGCAGTGTTTGACAGAAAGGCCTTCCGTCCATTCAC
CAACTACAGCATCCCTACCCGTGTCAACATCTCCTTCACCCTGTCTGCCATCCTGGGAGTGGATGCACA
GCTCCAGCTGCTGACATCATTCCTGTGGATGGATTTGGTATGGGACAATCCTTTCATTAATTGGAACCC
AAAAGAGTGTGTTGGCATCAATAAACTCACAGTATTAGCTGAAAACCTGTGGCTCCCAGACATCTTCAT
CGTGGAATCCATGGATGTGGATCAGACGCCTTCCGGTCTCACTGCCTATATCAGCAGTGAAGGTCGAAT
TAAGTATGATAAGCCAATGAGGGTGACCAGCATCTGTAAACTGGACATCTTCTACTTCCCTTTTGACCA
ACAGAACTGTACCTTCACCTTCAGTTCTTTCCTCTACACAGTGGACAGCATGCTGCTGGGCATGGACAA
GGAGGTGTGGGAGATCACAGACACGTCTCGCAAAGTCATCCAAACCCAGGGGGAGTGGGAGCTCTTGGG
CATCAACAAGGCCACCCCAAAGATGTCCATGGGCAACAACCTATATGACCAGATCATGTTTTATGTGGC
CATCAGGCGCAGGCCAAGCCTCTACATCATAAACCTGCTGGTGCCCAGTAGCTTTCTGGTTGCCATTGA
TGCCCTCAGCTTCTACCTGCCAGCAGAGAGCGAGAATCGTGCCCCATTCAAGATAACACTTCTGCTGGG
CTACAACGTCTTCCTGCTCATGATGAATGACTTGCTCCCTGCCAGTGGCACCCCCCTCATCAGTGTCTA
CTTCGCCCTGTGCCTGTCCCTGATGGTGGTCAGCCTGCTGGAGACCGTCTTCATTACCTACCTGCTGCA
CGTGGCCACCACCCAGCCCCCACCCATGCCTAGGTGGCTTCACTCCCTGCTGCTCCACTGCACCAGCCC
AGGGAGATGCTGTCCCACTGCGCCCCAGAAGGGAAATAAGGGCCTGGGTCTCACCCTCACCCACCTGCC
TGGCCCAAAGGAGCCGGGGGAGTTAGCAGGGAAGAAGCTGGGACCCAGAGAGACCGAGCCAGATGGGGG
CTCAGCATGGACAAAGACCCAGCTAATGGAGCTGTGGGTGCAGTTCAGCCACGCGATGGACACCCTGCT
CTTCCGCCTCTACCTGCTCTTCATGGCCTCCTCCATCCTTACTGTCATTGTCCTCTGGAACACCTAGGC
AGACATCCCCCCTCTCTGGCAAACAACAGCTTGGAGTTTCTGCTGGTCTTGGGCCAGCCGGACTCATTT
TCCTAATCTTAGCCACTTATCCCCAGTGACTACCATGTCCCCTTCTAAATTCCAAAGAATCCAACGCAG
CACTAGCAAGCAGGTTCAGGACAGCCCTGGACGATTTCCCGACCGCTGCTCAGGGTGGTCATTCCTGCT
CACCCTCAGTTTCCCTGAGGTACCACCTAACTCCTCACTCCCTGATCAATGGAAGTTCAGGTCAGTGGA
GTCTTTCCTTGATTGATCACCCCAATAAACAACTTTTCAGGGAAAAAAAAAAAAAAAAAAAAAAAAAAA
AAAAAAAAAAAAAAAAAAAA

FIGURE 2

[SEQ.ID.NO.:6] Nucleotide sequence for the coding region of 5-HT3-C is shown; 1341 [this does not include the TAG termination codon] bases.

```
ATGGAAGGAGGGTGGCCTGCAAGGCAGAGTGCCCTCCTCTGCCTCACTGTCAGTCTT
CTGCTTCAAGGAAGAGGCGACGCTTTTACCATCAATTGCTCAGGCTTTGACCAGCAT
GGGGTTGACCCTGCTGTCTTCCAAGCAGTGTTTGACAGAAAGGCCTTCCGTCCATTC
ACCAACTACAGCATCCCTACCCGTGTCAACATCTCCTTCACCCTGTCTGCCATCCTG
GGAGTGGATGCACAGCTCCAGCTGCTGACATCATTCCTGTGGATGGATTTGGTATGG
GACAATCCTTTCATTAATTGGAACCCAAAAGAGTGTGTTGGCATCAATAAACTCACA
GTATTAGCTGAAAACCTGTGGCTCCCAGACATCTTCATCGTGGAATCCATGGATGTG
GATCAGACGCCTTCCGGTCTCACTGCCTATATCAGCAGTGAAGGTCGAATTAAGTAT
GATAAGCCAATGAGGGTGACCAGCATCTGTAACCTGGACATCTTCTACTTCCCTTTT
GACCAACAGAACTGTACCTTCACCTTCAGTTCTTTCCTCTACACAGTGGACAGCATG
CTGCTGGGCATGGACAAGGAGGTGTGGGAGATCACAGACACGTCTCGCAAAGTCATC
CAAACCCAGGGGGAGTGGGAGCTCTTGGGCATCAACAAGGCCACCCCAAAGATGTCC
ATGGGCAACAACCTATATGACCAGATCATGTTTTATGTGGCCATCAGGCGCAGGCCA
AGCCTCTACATCATAAACCTGCTGGTGCCCAGTAGCTTTCTGGTTGCCATTGATGCC
CTCAGCTTCTACCTGCCAGCAGAGAGCGAGAATCGTGCCCCATTCAAGATAACACTT
CTGCTGGGCTACAACGTCTTCCTGCTCATGATGAATGACTTGCTCCCTGCCAGTGGC
ACCCCCCTCATCAGTGTCTACTTCGCCCTGTGCCTGTCCCTGATGGTGGTCAGCCTG
CTGGAGACCGTCTTCATTACCTACCTGCTGCACGTGGCCACCACCCAGCCCCCACCC
ATGCCTAGGTGGCTTCACTCCCTGCTGCTCCACTGCACCAGCCCAGGGAGATGCTGT
CCCACTGCGCCCAGAAGGGAAATAAGGGCCTGGGTCTCACCCTCACCCACCTGCCT
GGCCCAAAGGAGCCGGGGGAGTTAGCAGGGAAGAAGCTGGGACCCAGAGAGACCGAG
CCAGATGGGGCTCAGGATGGACAAAGACCCAGCTAATGGAGCTGTGGGTGCAGTTC
AGCCACGCGATGGACACCCTGCTCTTCCGCCTCTACCTGCTCTTCATGGCCTCCTCC
ATCCTTACTGTCATTGTCCTCTGGAACACCTAG
```

FIGURE 3

[SEQ.ID.NO.:9] The amino acid sequence of 5-HT3-C is shown (447 amino acids).

| | | | | |
|---|---|---|---|---|
| MEGGWPARQS | ALLCLTVSLL | LQGRGDAFTI | NCSGFDQHGV | DPAVFQAVFD |
| RKAFRPFTNY | SIPTRVNISF | TLSAILGVDA | QLQLLTSFLW | MDLVWDNPFI |
| NWNPKECVGI | NKLTVLAENL | WLPDIFIVES | MDVDQTPSGL | TAYISSEGRI |
| KYDKPMRVTS | ICNLDIFYFP | FDQQNCTFTF | SSFLYTVDSM | LLGMDKEVWE |
| ITDTSRKVIQ | TQGEWELLGI | NKATPKMSMG | NNLYDQIMFY | VAIRRRPSLY |
| IINLLVPSSF | LVAIDALSFY | LPAESENRAP | FKITLLLGYN | VFLLMMNDLL |
| PASGTPLISV | YFALCLSLMV | VSLLETVFIT | YLLHVATTQP | PPMPRWLHSL |
| LLHCTSPGRC | CPTAPQKGNK | GLGLTLTHLP | GPKEPGELAG | KKLGPRETEP |
| DGGSGWTKTQ | LMELWVQFSH | AMDTLLFRLY | LLFMASSILT | VIVLWNT |

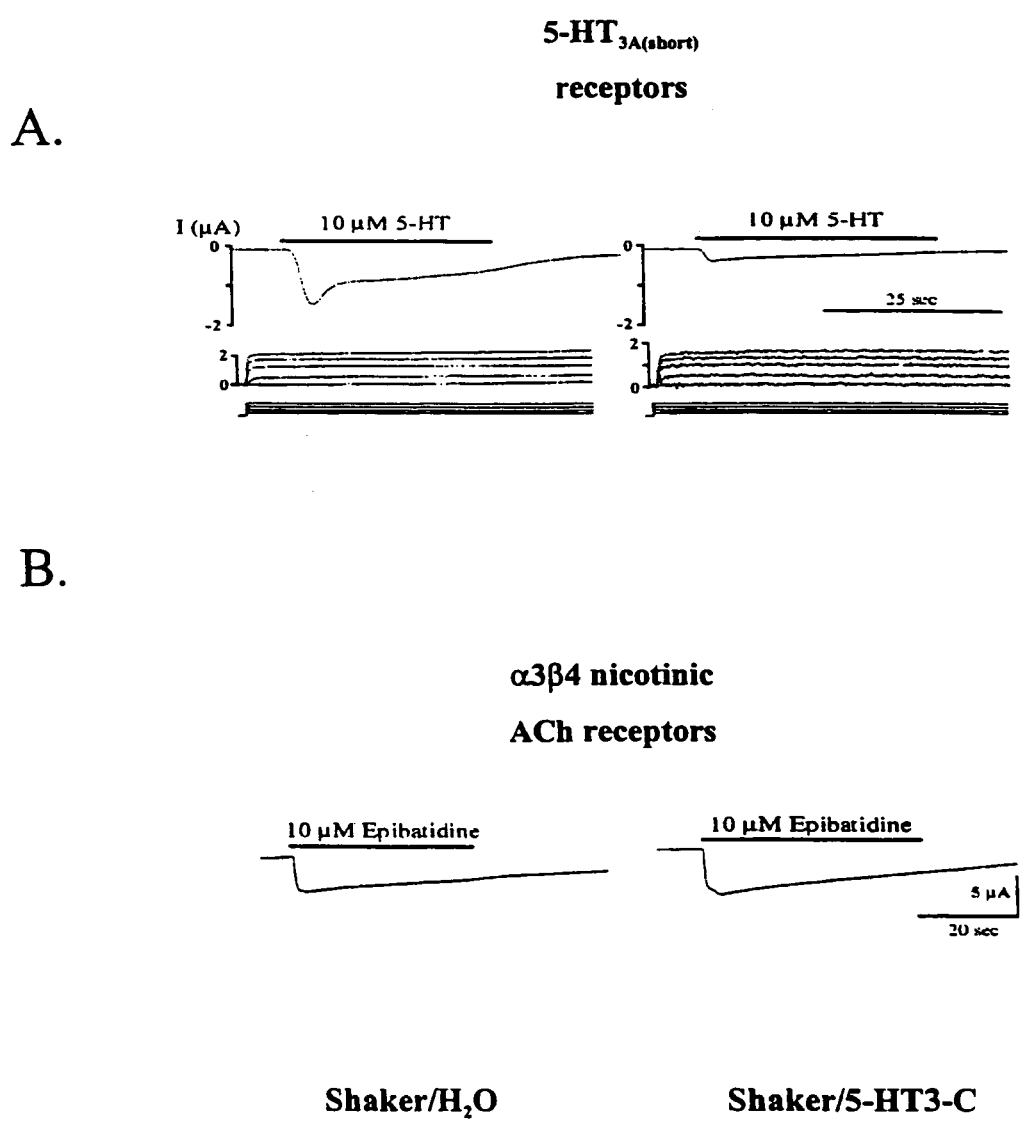

Figure 6b.

| Tissue or cell type | 5-HT$_{2C}$ (mean intensity) | 5-HT$_{1A}$ (mean intensity) |
|---|---|---|
| CD19+ B-cells | 501 +/- 42 (p < 0.005) | 66 +/- 10 (p<0.025) |
| Fibroblasts | 142 +/- 37 (p < 0.025) | 84 +/- 5 (p < 0.0005) |
| DRG | 110 +/- 10 (p < 0.01) | 140 +/- 10 (p < 0.0005) |
| Mammary gland | 102 +/- 13 (p < 0.0025) | 96 +/- 16 (p < 0.01) |
| Salivary gland | 96 +/- 4 (p < 0.0005) | 98 +/- 11 (p < 0.005) |
| Bone marrow | 94 +/- 3 (p < 0.0005) | 74 +/- 13 (p < 0.05) |
| Liver | 93 +/- 5 (p < 0.0005) | NS |
| Small airway epithelial cells | 92 +/-14 (p < 0.025) | NS |
| Stomach antrum | 90 +/- 5 (p < 0.001) | 110 +/- 40 (NS) |
| Olfactory bulb | 89 +/- 7 (p < 0.05) | 91 +/- 13 (NS) |
| Prostate | 86 +/- 7 (p < 0.0025) | 66 +/- 4 (p < 0.01) |
| Whole blood | 82 +/- 4 (p < 0.0005) | 50 +/- 10 (p < 0.05) |
| Thymus | 79 +/- 6 (p < 0.0005) | 56 +/- 4 (p < 0.0025) |
| Placenta | 78 +/- 11 (p < 0.01) | 53 +/- 4 (p < 0.025) |
| Small intestine | 78 +/- 3 (p < 0.0005) | 82 +/- 8 (p < 0.005) |
| Adrenal gland | 75 +/- 5 (p < 0.001) | NS |
| Pancreas | 74 +/- 4 (p < 0.001) | 125 +/- 34 (p < 0.05) |
| Lymph node | 74 +/- 7 (p < 0.001) | NS |
| Gallbladder | 74 +/- 10 (p < 0.001) | NS |
| Thyroid | 73 +/- 8 (p < 0.025) | 57 +/- 4 (p < 0.05) |
| Uterus | 72 +/- 3 (p < 0.0005) | 55 +/- 6 (p < 0.05) |
| Testis | 70 +/- 4 (p < 0.0005) | 56 +/- 4 (p < 0.01) |
| Hypothalamus | 69 +/- 10 (p < 0.025) | 80 +/- 12 (p < 0.05) |

FIGURE 6B Continued

| Tissue or cell type | 5-HT$_{2C}$ (mean intensity) | 5-HT$_{3A}$ (mean intensity) |
|---|---|---|
| Substantia nigra | 67 +/- 5 (p < 0.025) | NS |
| Amygdala | 65 +/- 6 (p < 0.05) | * |
| Bronchial smooth muscle cells | 46 +/- 3 (< 0.005) | NS |
| Trachea | 40 +/- 2 (p < 0.005) | 85 +/- 16 (p < 0.025) |

Values are the mean intensity of the labeled cRNA hybridizing to the cDNA microarray +/- S.E.M. The mean intensity for cRNAs from all tissues shown were significantly different (p value in parentheses) from 75% of the control-plant cDNA value. Data are averaged from 3-6 experiments. * 5-HT3-A receptor subunit is expressed in these tissues but at low abundance (Bufton et al., 1993; Sugita et al., 1992). NS= not significant.

HUMAN 5-HT3-C PROTEIN

This is a continuation of prior application U.S. Ser. No. 09/955,524, filed Sep. 12, 2001, now abandoned, which is a divisional of U.S. application Ser. No. 09/388,349, filed Sep. 1, 1999, now U.S. Pat. No. 6,365,370.

BACKGROUND OF THE INVENTION

Serotonin (5-hydroxytryptamine, 5-HT) is a multifunctional chemical transmitter that signals though cell surface receptors. At least fourteen subtypes of serotonin receptors have been defined pharmacologically (Julius, 1996). Thirteen of the fourteen known receptors are G-protein coupled receptors and the only known ionotropic 5-HT receptor, the type 3 5-HT3 receptor, is a fast activating, ligand gated non-selective cation channel unique among known monoamine receptors (Derkach et al., 1989). The 5-HT3 receptor is exclusively localized on neurons in the central (Waeber et al., 1989; Yakel et al., 1991) and peripheral (Fozard, 1984) nervous systems. Activation of the 5-HT3 receptor leads to membrane depolarization and an increase in intracellular $Ca^{2+}$. The 5-HT3 receptor is the target of antagonists (granisetron and ondansetron) selective against the nausea induced by cytotoxic chemotherapy and general anesthesia (Gralla, 1998). There is some evidence that serotonin 5-HT3 receptors are important in pain reception, anxiety, cognition, cranial motor neuron activity, sensory processing, modulation of affect, and the behavioral consequences of drug abuse (Greenshaw and Silverstone, 1997; Lanbert et al., 1995; Passani and Corradetti, 1996).

There are two known subunits for the human 5-HT3 receptor: 5-HT3-A (Belelli et al., 1995; Miyake et al., 1995) and 5-HT3-B (Davies et al., 1999). They have structural and functional similarities with nicotinic, GABA-ergic and other ligand gated ion channels (Barnard, 1996; Gurley and Lanthorn, 1998; Maricq et al., 1991). The modifier subunit 5-HT3-B for the serotonin 5-HT3 receptor can explain certain observations that 5-HT3 receptors from a variety of preparations have distinct pharmacological, kinetic, permeation and voltage-dependent properties (Peters et al., 1992) (Dubin et al., manuscript submitted to JBC). However, biochemical evidence suggests that 5-HT3 receptors may exist as heteromultimers composed of more than 2 subunits. Receptors purified from a variety of sources by affinity chromatography usually reveal at least 2 major protein bands with molecular masses in the order of 54 and 38 kDa (Lambert et al., 1995). The 5-HT3-A receptor corresponds to the former (Turton et al., 1993). Affinity purified 5-HT3 receptor solubilized from pig cerebral cortex is composed of at least 3 separable components, based on silver staining of proteins on denaturing gels (Fletcher and Barnes, 1997). A number of these protein bands are not recognized by specific antibodies directed against the recombinant 5-HT3-A subunit (Fletcher and Barnes, 1997), and their sizes are too large (52–71 kDa) to be considered as degraded 5-HT3-A fragments (Fletcher and Barnes, 1998).

Heteromeric assembly of subunits often produces channels with altered function compared to homomeric charnels. An increasing number of subunits have been reported to be electrically silent when expressed alone but profoundly inhibit the function of specific classes of channels in co-expression studies (Kv8, Kv9, Kir1.3) (Hugnot et al., 1996; Salinas et al., 1997; Salinas et al., 1997; Shuck et al., 1997; Stocker et al., 1999). Like 5-HT3 receptors, voltage-gated potassium channels are heteromers of similar subunits (Jan and Jan, 1997). Kv8.1 and members of the Kv9 family have the capability to abolish the functional expression of specific potassium channel family members when co-expressed at high levels (Hugnot et al., 1996; Salinas et al., 1997; Salinas et al., 1997; Stocker et al., 1999). Immunoprecipitation experiments reveal co-assembly of Kv8.1 with Kv2 (Hugnot et al., 1996). Kv8.1 does not appear to reach the plasma membrane when expressed alone (Salinas et al., 1997) and homomeric assembly of Kv9 subunits does not occur (Stocker et al., 1999).

Functional expression of the inward potassium channel Kir1.3 in *Xenopus oocytes* was not detectable, however, co-expression of Kir1.3 with either Kir1.1 or Kir1.2 reduced the currents resulting from expression of these inward-rectifier subunits alone, consistent with a negative influence on Kir1.1 and Kir1.2 expression (Shuck et al., 1997).

A number of naturally occurring mutant channels exist that reduce channel function. In one form of episodic ataxia, mutations in the gene encoding Kv1.1 abolish the function of wild-type Kv1.1 subunits (Mathur et al., 1999; Zerr et al., 1998). In the LQT1 form of long QT syndrome KvLQT1 mutations A177P or T311I have a dominant negative effect on currents produced by KvLQT1 with or without mink when channel subunit combinations are expressed in *Xenopus oocytes* (Shalaby et al., 1997). Expression of these KvLQT1 mutants either individually or in combination yielded inactive channels when expressed individually and inhibit wild-type KvLQT1 currents in a dominant-negative fashion.

A naturally occurring HERG mutant G601S is a hypomorphic mutation (ie., a specific mutant form of a gene that exhibits function qualitatively similar to the normal state but with quantitatively less function), resulting in a reduced current amplitude and represents a novel mechanism underlying LQT2 (Furutani et al., 1999).

A wide range of single channel conductances has been reported for the 5-HT3-A receptor subunit and endogenous 5-HT3 receptors in native cells. This variation is attributable in part to heteromeric formation of 5-HT3-A with 5-HT3-B subunits (Davies et al., 1999). Homomeric receptors revealed a sub-pS conductance whereas heteromeric receptors displayed large single channel conductance (16 pS) (Davies et al., 1999). Modulation of the conductance of 5-HT3 receptors has been reported. Van Hooft and colleagues have shown that the conductance of 5-HT3 receptors in NIE-115 cells is dependent on phosphorylation conditions (Van Hooft and Vijverberg, 1995).

An unmet need in this field is the ability to reconstitute a recombinant expression system that fully mimics the 5-HT3 receptor complex in natural tissue, likely due to incomplete receptor complexes localized at the cell surface. By creating a more physiologically relevant model of the 5-HT3 receptor complex using in vitro systems, it will be easier to develop and test new therapeutic compounds for treatment of diseases associated with the 5-HT3 serotonin receptor. This unmet need has been met by the isolation and characterization of a novel 5-HT3 receptor subunit cDNA molecule, hereafter termed 5-HT3-C. Using a recombinant expression system, functional DNA molecules encoding the subunit have been isolated. The biological and structural properties of this protein are disclosed, as is the amino acid and nucleotide sequence. The recombinant protein is useful to identify modulators of the 5-HT3 serotonin receptor complex, and to reconstitute a more realistic physiological 5-HT3 receptor response in recombinant systems. Co-expression of the 5-HT3-A with the 5-HT3-C subunit reduces the biological function of the 5-HT3-A receptor for some known modulators of 5-HT3 receptors. Modulators identified in the assay disclosed herein are useful as therapeutic agents. The recombinant DNA molecules, and portions thereof, are useful for isolating homologues of the DNA molecules, identifying and isolating genomic equivalents of the DNA molecules, and identifying, detecting or isolating mutant forms of the DNA molecules.

SUMMARY OF THE INVENTION

A DNA molecule encoding a human subunit with homology to the 5-HT3-A serotonin receptor has been cloned and when co-expressed with the short form of the human serotonin 5-HT3-A receptor modifies the function of the 5-HT3 receptor. Using a recombinant expression system, functional DNA molecules encoding the human serotonin 5-HT3 receptor modifier protein (5-HT3-C) have been isolated. The biological and structural properties of these proteins are disclosed, as is the amino acid and nucleotide sequence. The recombinant protein is useful to identify modulators of human 5-HT3 receptors composed of both 5-HT3 receptors and the modifier subunit (5-HT3-C). Modulators identified in the assay disclosed herein are useful as therapeutic agents for conditions including, but are not limited to, nausea, depression, anxiety, psychoses (for example schizophrenia), urinary continence, Huntington's chorea, tardive dyskinesia, Parkinson's disease, obesity, hypertension, migraine, Gilles de la Tourette's syndrome, sexual dysfunction, drug addiction, drug abuse, cognitive disorders, learning, Alzheimer's disease, cerebral coma, senile dementia, obsessive-compulsive behavior, panic attacks, pain, social phobias, eating disorders and anorexia, cardiovascular and cerebrovascular disorders, non-insulin dependent diabetes mellitus, hyperglycemia, constipation, arrhythmia, disorders of the neuroendocrine system, stress, and spasticity, as well as acid secretion, ulcers, airway constriction, asthma allergy, inflammation, and prostate dysfunction. The recombinant DNA molecules and portions thereof, are useful for isolating homologues of the DNA molecules, identifying and isolating genomic equivalents of the DNA molecules, gene therapy applications, and identifying, detecting or isolating mutant forms of the DNA molecules.

BRIEF DESCRIPTION OF THE DRAWINGS

FIG. 1—[SEQ.ID.NO.:5] Nucleic Acid sequence of the human 5-HT3-C (full sequence including untranslated regions); 1745 bases. (34 bases of 5' UTR; 367 bases of 3' UTR)

FIG. 2—[SEQ.ID.NO.:6] Nucleotide sequence for the coding region of 5-HT3-C is shown; 1341 bases.

FIG. 3—[SEQ.ID.NO.:7] The amino acid sequence of human 5-HT3-C is shown (447 amino acids).

FIG. 4—Functional expression of human 5-HT3-C together with 5-HT3-A receptor in Xenopus oocytes: 5-HT3-C decreases the magnitude of 5-HT3-A currents elicited by the agonist 5-HT but not the magnitude of epibatidine-induced currents in nicotinic ACh receptor α3β4-co-injected oocytes. (a.) Oocytes were injected with 0.33 ng 5-HT3-A together with 0.025 ng of a Shaker N-terminal deletion mutant and either water or 0.67 ng 5-HT3-C cRNA. Top: currents elicited by 10 µM 5-HT. Bottom: currents activated by a family of depolarizing voltage steps (40 to +50 mV in 30 mV increments from a holding potential of −70 mV) indicate that potassium channel expression is similar in both sets of oocytes. Oocytes were tested 6 days after injection. (b.) Oocytes were injected with 0.30 ng α3 and 0.25 ng β4 nicotinic ACh receptor subunits together with either water or 0.067 ng 5-HT3-C cRNA. Oocytes were tested 6 days after injection for their responsiveness to 10 µM epibatidine. 5-HT3-C had no effect on α3β4 mediated currents. The reversal potentials for 5-HT-induced currents in oocytes expressing both 5-HT3-A and 5-HT3-C (1:5 ratio) were similar to 5-HT3-A receptors indicating that the decrease in 5-HT-induced current is not due to a shift in ion permeability.

Figure 5:
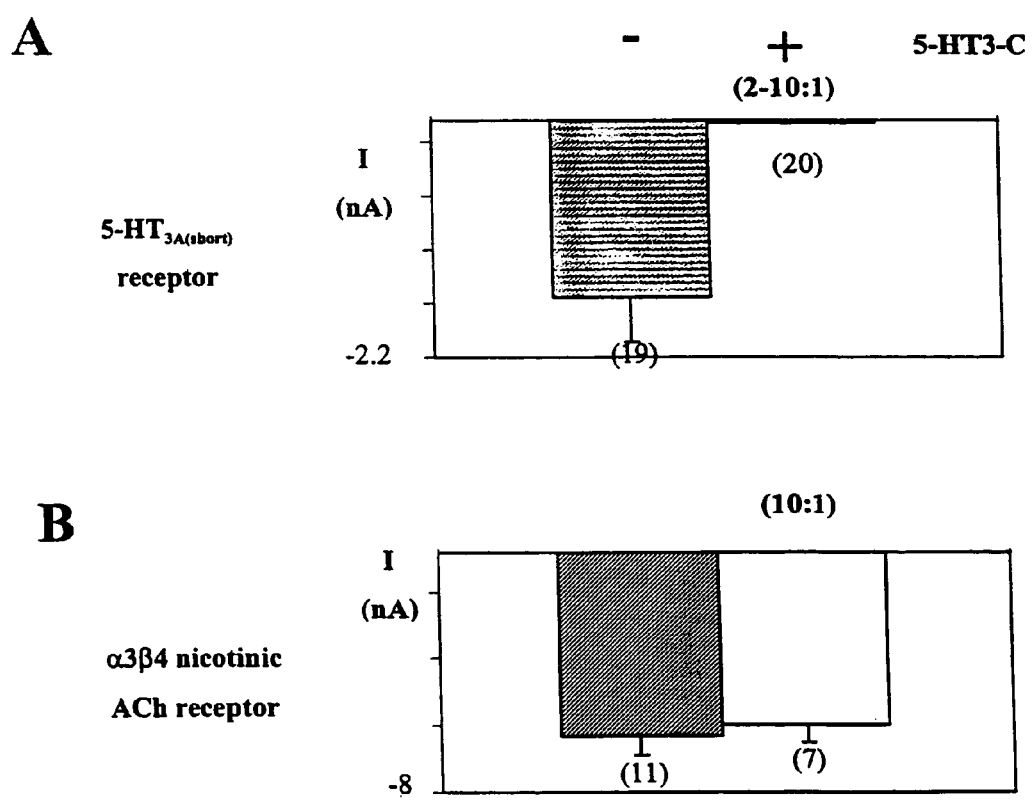
FIG. 5—Quantification and specificity of the modulatory effect of human 5-HT3-C in oocytes is shown. (a.) Peak response elicited by 10 µM 5-HT exposure to oocytes expressing 5-HT3-A (short) (0.33 ng) with (clear; n=5) and without (hatched; n=4) 5-HT3-C (0.67 ng). (b.) Peak response to 10 µM epibatidine exposure to oocytes expressing the nicotinic ACh receptor α3β4 (0.25 ng each) with (clear; n=8) and without (hatched; n=9) 5-HT3-C (3.35 ng).
Figures 6, 6A:
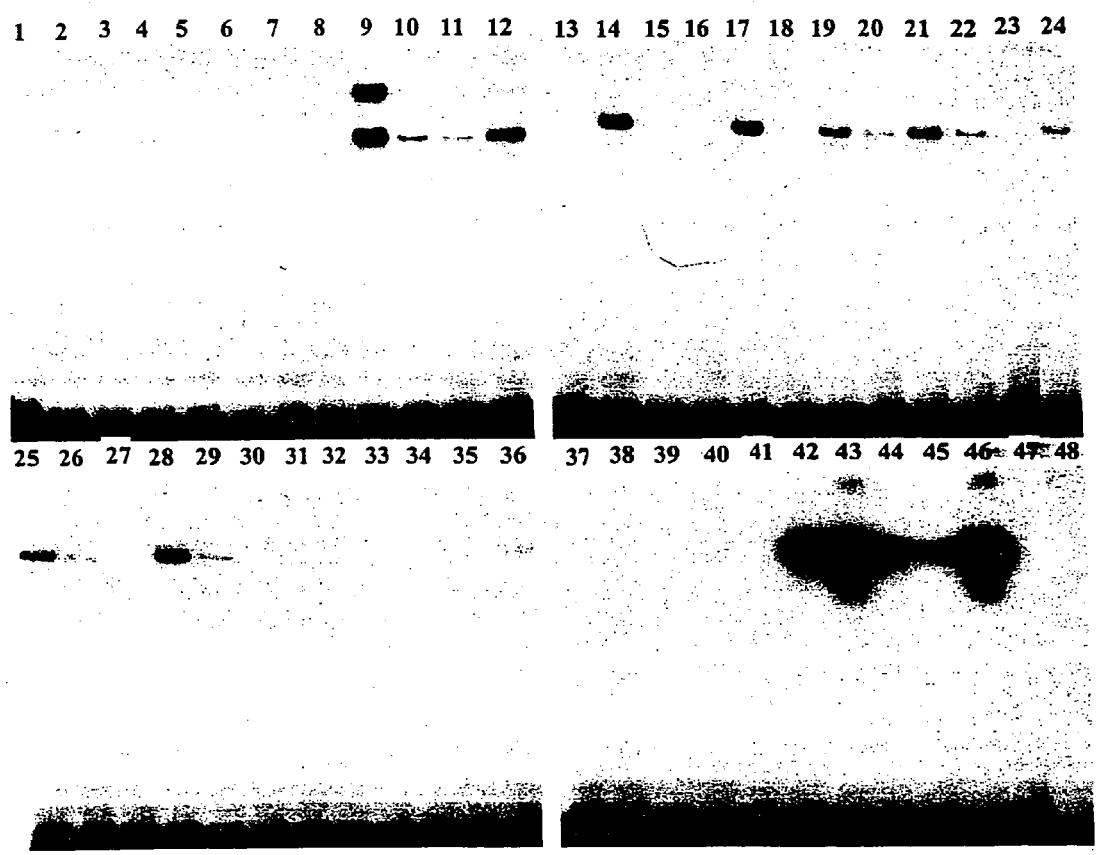
FIG. 6—PANEL A [FIG. 6A]. The PCR-based tissue distribution of the human 5-HT3-C is shown. Lanes are labeled as indicated: 1, Amygdala; 2, Bone marrow; 3, Brain; 4, Cerebellum; 5 Heart; 6, Hippocampus; 7, Kidney; 8, Liver, 9, Lung; 10, Pancreas; 11, Placenta; 12, Prostate; 13, Skeletal muscle; 14, small intestine; 15, spleen; 16, spinal cord; 17, stomach; 18, Thalamus; 19, Testis; 20, Thymus; 21, Uterus; 22, Adrenal gland; 23, Caudate; 24, Lymph node; 25, Mammary Gland; 26, Salivary gland; 27, Substantia nigra; 28, Thyroid; 29, Trachea; 30, Negative control; 31, Spleen library; 32, Thalamus library; 33, Placenta library; 34, Heart library; 35, Liver library; 36, Lung library; 37 uterus library; 38, pituitary library; 39, spinal cord library; 40, bone marrow library; 41, hippocampus library; 42, dorsal root ganglion library; 43, small intestine library; 44, hypothalamus library; 45, cerebral cortex library; 46, cerebellum library; 47 and 48, negative controls (no DNA template).

PANEL B [FIG. 6B]. Microarray analysis 5-HT3-C and 5-HT3-A mRNAs are expressed in B-cells, fibroblasts, dorsal root ganglia, mammary, salivary glands, bone marrow, spleen, prostate, Skeletal muscle, thymus, Placenta, thyroid, uterus, testis, hypothalamus, hippocampus, amygdala, trachea and small intestine. Consistent with the labeling pattern shown in FIG. 6a, 5-HT3-C and 5-HT3-A mRNA were detected in spleen, small and large intestine and CD14+ monocytes using microarray hybridization techniques.

DETAILED DESCRIPTION

Serotonin is a biogenic amine transmitter that functions in some capacity in many physiological and pathophysiological conditions. Serotonin acts as a neurotransmitter and neuromodulator in the central and peripheral nervous systems, mediates inflammatory and allergic responses, regulates airway function, controls acid secretion in the stomach, regulates cardiovascular function as well as arterial and venous responses and is likely involved in to processes yet to be determined. The serotonin receptors that mediate these include the ligand-gated 5-HT3 receptor. Overlap of 5-HT3-A and 5-HT3-C receptor expression suggests that the putative heteromultimer is involved in central and peripheral nervous system [DRG] as well as small intestine, thymus, prostate and uterine function.

The present invention relates to DNA encoding human 5-HT3-C, which was isolated from a cDNA library from human lung. The human 5-HT3-C, as used herein, refers to protein, which can specifically decrease or abolish the function of 5-HT3-A receptors.

The complete amino acid sequence of the human 5-HT3-C was not known, nor was the complete nucleotide sequence encoding human 5-HT3-C known prior to the present invention.

The present invention provides a mechanism to diminish 5-HT3 receptor function. The present invention shows that 5-HT3-C specifically alters functional expression of the 5-HT3-A without affecting nicotinic ACh receptor α3β4 function. The physiological significance of the novel findings reported herein include the ability of cells co-expressing 5-HT3-C and 5-HT3-A to be less sensitive to 5-HT than cells expressing homomeric 5-HT3-A(short) or 5-HT3-A (short)/5-HT3-C heteromeric receptors. These alterations in receptor-mediated current has profound effects on 5-HT activation of neuronal excitability. It is predicted that a variety of cells and cell types will contain the human 5-HT3-C. Vertebrate cells capable of producing human 5-HT3-C include, but are not limited to lung, prostate, small intestine, stomach, B-cells, fibroblasts, dorsal root ganglia, mammary gland, salivary gland, bone marrow, lymph node, thymus, placenta, thyroid, uterus, testis, liver, hypothalamus, amygdala, and trachea as well as bronchial smooth muscle cells, gallbladder, small airway epithelial cells and olfactory bulb (FIG. 6).

Other cells and cell lines may also be suitable for use to isolate human 5-HT3-C cDNA. Selection of suitable cells may be done by screening for mRNA encoding the 5-HT3-C subunit using RT-PCR and microarray technology. Human 5-HT3-C activity can be monitored before and after incubation of cells with antisense sequences for 5-HT3-C by performing a $^3$H-[mCPBG] or $^3$H-[Y25130 or MDL 72222] binding assay in the presence of 5-HT3-A receptor (Steward et al., 1993), by direct measurement of a $Ca^{+2}$ influx using the $Ca^{+2}$ sensitive dyes (Kuntzweiler et al., 1998), or by net ion flux using voltage clamp techniques (Hamill et al., 1981). After antisense treatment, the response to 5-HT will be enhanced in cells expressing both 5-HT3-A and 5-HT3-C. Cells that possess human 5-HT3-C activity in this assay may be suitable for the isolation of human 5-HT3-C DNA or mRNA. Selection of suitable cells may be done by screening for antibody binding to the cell surface for an antibody specifically reactive to 5-HT3-C. Cells that possess said antibody binding may be suitable for the isolation of human 5-HT3-C DNA or mRNA.

Any of a variety of procedures known in the art may be used to molecularly clone human 5-HT3-C DNA. These methods include, but are not limited to, direct functional expression of the human 5-HT3-C genes following the construction of a human 5-HT3-C—containing cDNA library in an appropriate expression vector system. Another method is to screen human 5-HT3-C—containing cDNA library constructed in a bacteriophage or plasmid shuttle vector with a labelled oligonucleotide probe designed from the amino acid sequence of the human 5-HT3-C subunits. An additional method consists of screening a human 5-HT3-C —containing cDNA library constructed in a bacteriophage or plasmid shuttle vector with a partial cDNA encoding the human 5-HT3-C protein. This partial cDNA is obtained by the specific PCR amplification of human 5-HT3-C DNA fragments through the design of degenerate oligonucleotide primers from the amino acid sequence of the purified human 5-HT3-C protein.

Another method is to isolate RNA from human 5-HT3-C—producing cells and translate the RNA into protein via ari in vitro or an in vivo translation system. Translation of the RNA into a peptide a protein will result in the production of at least a portion of the human 5-HT3-C protein which an be identified by, for example, immunological reactivity with an anti-human 5-HT3-C antibody or by biological activity of human 5-HT3-C protein. In this method, pools of RNA isolated from human 5-HT3-C—producing cells can be analyzed for the presence of an RNA that encodes at least a portion of the human 5-HT3-C protein. Further fractionation of the RNA pool can be done to purify the human 5-HT3-C RNA from non-human 5-HT3-C RNA. The peptide or protein produced by this method may be analyzed to provide amino acid sequences which in turn are used to provide primers for production of human 5-HT3-C cDNA, or the RNA used for translation can be analyzed to provide nucleotide sequences encoding human 5-HT3-C and produce probes for this production of human 5-HT3-C cDNA. This method is known in the art and can be found in, for example, Maniatis, T., Fritsch, E. F., Sambrook, J. in Molecular Cloning: A Laboratory Manual, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating human 5-HT3-C —encoding DNA. Other types of libraries include, but are not limited to, cDNA libraries derived from other cells, from organisms other than human, and genomic DNA libraries that include YAC (yeast artificial chromosome) and cosmid libraries.

It is readily apparent to those skilled in the art that suitable cDNA libraries may be prepared from cells or cell lines which have human 5-HT3-C activity. The selection of cells or cell lines for use in preparing a cDNA library to isolate human 5-HT3-C cDNA may be done by first measuring cell-associated human 5-HT3-C activity using the measurement of human 5-HT3-C —associated biological activity or a-human 5-HT3-C —5-HT3-A receptor ligand binding assay [$^3$H-mCPBG] (Steward et al., 1993) or $^3$H-[Y25130 or MDL 72222] binding.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor Laboratory, Cold Spring Harbor, N.Y., 1989).

It is also readily apparent to those skilled in the art that DNA encoding human 5-HT3-C may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

In order to clone the human 5-HT3-C gene by the above methods, the amino acid sequence of human 5-HT3-C may be necessary. To accomplish this, human 5-HT3-C protein may be purified and partial amino acid sequence determined by automated sequencers. It is not necessary to determine the entire amino acid sequence, but the linear sequence of two regions of 6 to 8 amino acids from the protein is determined for the production of primers for PCR amplification of a partial human 5-HT3-C DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the human 5-HT3-C sequence but will be capable of hybridizing to human 5-HT3-C DNA even in the presence of DNA oligonucleotides with mismatches. The mismatched DNA oligonucleotides may still sufficiently hybridize to the human 5-HT3-C DNA to permit identification and isolation of human 5-HT3-C encoding DNA. DNA isolated by these methods can be used to screen DNA libraries from a variety of cell types, from invertebrate and vertebrate sources, and to isolate homologous genes.

Purified biologically active human 5-HT3-C may have several different physical forms. Human 5-HT3-C may exist as a full-length nascent or unprocessed polypeptide, or as partially processed polypeptides or combinations of processed polypeptides. The full-length nascent human 5-HT3-C polypeptide may be posttranslationally modified by specific proteolytic cleavage events that result in the formation of fragments of the full-length nascent polypeptide. A fragment, or physical association of fragments may have the full biological activity associated with human 5-HT3-C however, the degree of human 5-HT3-C activity may vary between individual human 5-HT3-C fragments and physically associated human 5-HT3-C polypeptide fragments.

The cloned human 5-HT3-C DNA obtained through the methods described herein may be recombinantly expressed by molecular cloning into an expression vector containing a suitable promoter and other appropriate transcription regulatory elements, and transferred into prokaryotic or eukaryotic host cells to produce recombinant human 5-HT3-C protein. Techniques for such manipulations are fully described in Maniatis, T, et al., supra and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli*, blue-green algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant human 5-HT3-C in mammalian cells. Commercially available mammalian expression vectors which may be suitable for recombinant human 5-HT3-C expression, include but are not limited to, pMAMneo (Clontech), pcDNA3 (InVitrogen), pMCIneo (Stratagene), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRSVgpt (ATCC 37199), pRSV-neo (ATCC 37198), pSV2-dhfr (ATCC 37146), pUCTag (ATCC 37460), and 1ZD35 (ATCC 37565).

A variety of bacterial expression vectors may be used to express recombinant human 5-HT3-C in bacterial cells. Commercially available bacterial expression vectors that may be suitable for recombinant human 5-HT3-C expression include, but are not limited to pET vectors (Novagen) and pQE vectors (Qiagen).

A variety of fungal cell expression vectors may be used to express recombinant human 5-HT3-C in fungal cells such as yeast. Commercially available fungal cell expression vectors which may be suitable for recombinant human 5-HT3-C expression include but are not limited to pYES2 (InVitrogen) and *Pichia* expression vector (InVitrogen).

A variety of insect cell expression vectors may be used to express recombinant human 5-HT3-C in insect cells. Commercially available insect cell expression vectors that may be suitable for recombinant expression of human 5-HT3-C include but are not limited to pBlueBacII (InVitrogen).

DNA encoding human 5-HT3-C may be cloned into an expression vector for expression in a recombinant host cell. Recombinant host cells may be prokaryotic or eukaryotic, including but not limited to bacteria such as *E. coli* fungal cells such as yeast, mammalian cells including but not limited to cell lines of human, bovine, porcine, monkey and rodent origin, and insect cells including but not limited to *drosophila* and silkworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-KI (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce human 5-HT3-C protein. Identification of human 5-HT3-C expressing host cell clones may be done by several means, including but not limited to immunological reactivity with anti-human 5-HT3-C antibodies, and the presence of host cell-associated human 5-HT3-C activity.

Expression of human 5-HT3-C DNA may also be performed using in vitro produced synthetic mRNA. Synthetic mRNA or mRNA isolated from human 5-HT3-C producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being generally preferred.

To determine the human 5-HT3-C DNA sequence(s) that yields optimal levels of human 5-HT3-C activity and/or human 5-HT3-C protein, human 5-HT3-C DNA molecules including, but not limited to, the following can be constructed: the full-length open reading frame of the human 5-HT3-C cDNA encoding the 50.2 kDa protein from approximately base 35 to approximately base 1376 (these numbers correspond to first nucleotide of the first methionine and the last nucleotide before the first stop codon) and several constructs containing portions of the cDNA encoding human 5-HT3-C protein. All constructs can be designed to contain none, all or portions of the 5' or the 3' untranslated region of human 5-HT3-C cDNA. The levels of protein expression can be determined following the introduction, both singly and in combination, of these constructs into appropriate host cells. Following determination of the human 5-HT3-C DNA cassette yielding optimal expression in transient assays, this human 5-HT3-C DNA construct is transferred to a variety of expression vectors, for expression in host cells including, but not limited to, mammalian cells, baculovirus-infected insect cells, E. coli, and the yeast S. cerevisiae.

Host cell transfectants and microinjected oocytes may be used to assay both the levels of human 5-HT3-C activity and levels of human 5-HT3-C protein by the following methods. In the case of recombinant host cells, this involves the co-transfection of one or possibly two or more plasmids, containing the human 5-HT3-C DNA encoding one or more fragments or subunits and the 5-HT3-A receptor or transfection of the human 5-HT3-C protein into human cell lines expressing the 5-HT3-A receptor. In the case of oocytes, this involves the co-injection of synthetic RNAs for human 5-HT3-C and 5-HT3-A receptor proteins. Following an appropriate period of time to allow for expression, cellular protein is metabolically labelled with, for example $^{35}$S-methionine for 24 hours, after which cell lysates and cell culture supernatants are harvested and subjected to immunoprecipitation with polyclonal antibodies directed against the human 5-HT3-C protein.

Other methods for detecting human 5-HT3-C activity involve the direct measurement of human 5-HT3-C activity in whole cells transfected with human 5-HT3-A receptor with or without 5-HT3-C cDNA or oocytes injected with human 5-HT3-A receptor and 5-HT3-C mRNA. Human 5-HT3-C activity is measured by specific ligand binding and biological characteristics of the host cells expressing human 5-HT3-C DNA. In the case of recombinant host cells expressing human 5-HT3-A receptor and human 5-HT3-C, patch voltage clamp techniques can be used to measure receptor activity and quantitate human 5-HT3-C protein. In the case of oocytes patch clamp as well as two-electrode voltage clamp techniques can be used to measure the decay rate of agonist-induced currents or agonist dose response.

Levels of human 5-HT3-C protein in host cells are quantitated by immunoaffinity. Cells expressing h5-HT3-C can be assayed for the number of cell surface receptor molecules expressed by measuring the amount of radioactive mCPBG or Y25130 or MDL72222 binding or labeled antibodies, which are specific for the 5-HT3-C subunit, to the cell membranes. Human 5-HT3-C—specific affinity beads or human 5-HT3-C—specific antibodies are used to isolate for example $^{35}$S-methionine labelled or unlabelled human 5-HT3-C protein. Labelled human 5-HT3-C protein is analyzed by SDS-PAGE. Unlabelled human 5-HT3-C protein is detected by Western blotting, ELISA or RIA assays employing human 5-HT3-C specific antibodies.

Because the genetic code is degenerate, more than one codon may be used to encode a particular amino acid, and therefore, the amino acid sequence can be encoded by any of a set of similar DNA oligonucleotides. Only one member of the set will be identical to the human 5-HT3-C sequence but will be capable of hybridizing to human 5-HT3-C DNA even in the presence of DNA oligonucleotides with mismatches under appropriate conditions. Under alternate conditions, the mismatched DNA oligonucleotides may still hybridize to the human 5-HT3-C DNA to permit identification and isolation of human 5-HT3-C encoding DNA.

DNA encoding human 5-HT3-C from a particular organism may be used to isolate and purify homologues of human 5-HT3-C from other organisms. To accomplish this, the first human 5-HT3-C DNA may be mixed with a sample containing DNA encoding homologues of human 5-HT3-C under appropriate hybridization conditions. The hybridized DNA complex may be isolated and the DNA encoding the homologous DNA may be purified therefrom.

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein that does not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of human 5-HT3-C is a compound that possesses a biological activity (either functional or structural) that is substantially similar to the biological activity of human 5-HT3-C. The term "functional derivatives" is intended to include the "fragments," "variants," "degenerate variants," "analogs" and "homologues" or to "chemical derivatives" of human 5-HT3-C. The term "fragment" is meant to refer to any polypeptide subset of human 5-HT3-C. The term "variant" is meant to refer to a molecule substantially similar in structure and function to either the entire human 5-HT3-C molecule or to a fragment thereof. A molecule is "substantially similar" to human 5-HT3-C if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire human 5-HT3-C molecule or to a fragment thereof.

Following expression of human 5-HT3-C in a recombinant host cell, human 5-HT3-C protein may be recovered to provide human 5-HT3-C in active form. Several serotonin 5-HT3-A receptor purification procedures are available and suitable for use (Fletcher and Barnes, 1997; Fletcher et al., 1998; Lummis and Martin, 1992; Miller et al., 1992). As described above for purification of human 5-HT3-C from natural sources, recombinant human 5-HT3-C may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant human 5-HT3-C can be separated from other cellular proteins by use of an immunoaffinity column made with monoclonal or polyclonal antibodies specific for full length nascent human 5-HT3-C, polypeptide fragments of human 5-HT3-C or human 5-HT3-C subunits.

Monospecific antibodies to human 5-HT3-C are purified from mammalian antisera containing antibodies reactive against human 5-HT3-C or are prepared as monoclonal antibodies reactive with human 5-HT3-C using the technique of Kohler and Milstein, *Nature* 256: 495–497 (1975). Monospecific antibody as used herein is defined as a single antibody species or multiple antibody species with homogenous binding characteristics for human 5-HT3-C. Homogenous binding as used herein refers to the ability of the antibody species to bind to a specific antigen or epitope, such as those associated with the human 5-HT3-C, as described above. Human 5-HT3-C specific antibodies are raised by immunizing animals such as mice, rats, guinea pigs, rabbits, goats, horses and the like, with rabbits being preferred, with an appropriate concentration of human 5-HT3-C either with or without an immune adjuvant.

Preimmune serum is collected prior to the first immunization. Each animal receives between about 0.01 mg and about 100 mg of peptide encoding a fragment of human 5-HT3-C associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of human 5-HT3-C peptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) reactive with human 5-HT3-C are prepared by immunizing inbred mice, preferably Balb/c, with human 5-HT3-C peptide. The mice are immunized by the IP or SC route with about 0.01 mg to about 1.0 mg, preferably about 1 mg, of human 5-HT3-C peptide in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.01 to about 1.0 mg of human 5-HT3-C polypeptide in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp 2/0, with Sp 2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and ammopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using human 5-HT3-C peptide as the antigen. The culture fluids are also tested in the Ouchterlony precipitation assay to determine the isotype of the mAb. Hybridoma cells from antibody positive wells are cloned by a techniques such as the soft agar technique MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-human 5-HT3-C mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of human 5-HT3-C in body fluids or tissue and cell extracts.

It is readily apparent to those skilled in the art that the above described methods for producing monospecific antibodies may be utilized to produce antibodies specific for human 5-HT3-C polypeptide fragments, or full-length nascent human 5-HT3-C polypeptide, or the individual human 5-HT3-C subunits. Specifically, it is readily apparent to those skilled in the art that monospecific antibodies may be generated which are specific for only the human 5-HT3-C subunit or the fully functional receptor.

Human 5-HT3-C antibody affinity columns can be made by adding the antibodies to Affigel-10 (Bio-Rad), a gef support which is activated with N-hydroxysuccinimide esters such that the antibodies form covalent linkages with the agarose gel bead support. The antibodies are then coupled to the gel via amide bonds with the spacer arm. The remaining activate esters are then quenched with ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing human 5-HT3-C subunits are slowly passed through the column. The column is then washed with phosphate buffered saline until the optical density ($A_{280}$) falls to background, then the protein is eluted with 0.23 M glycine-HCl (pH 2.6). The purified human 5-HT3-C protein is then dialyzed against phosphate buffered saline.

DNA clones, termed p5HT3CR, are identified which encode proteins that, when expressed in any recombinant host, including but not limited to mammalian cells or insect cells or bacteria form a receptor that becomes insensitive to serotonin when co-expressed with 5-HT3-A (short) receptor subunits. The expression of human 5-HT3-C DNA results in the reconstitution of the properties observed in oocytes injected with human 5-HT3-C —encoding poly $(A)^+$ RNA together with 5-HT3-A receptor subunits. These include: reduction of the 5-HT-, mCPBG- and 1-PBG-induced responses compared to those observed for 5-HT3-A homomultimers.

One way to understand which serotorin receptors are involved in these processes is to develop chemical modulators of the receptors as research tools and therapeutic entities. Recombinant host cells expressing the human serotonin 5HT3-A and human 5-HT3-C receptors can be used to provide materials for a screening method to identify such agonists and antagonists. As such, this invention of the human serotonin 5-HT3-C subunit directly teaches a way to identify new agonists and antagonists that may prove useful as research tools or may be used as therapeutics to treat disorders directly or indirectly involving serotonin receptors.

The present invention is also directed to methods for screening for compounds that modulate the expression of DNA or RNA encoding human 5-HT3-C as well as the function of human 5-HT3-C protein in vivo. Compounds that modulate these activities may be DNA, RNA, peptides, proteins, or non-proteinaceous organic molecules. Compounds may modulate by increasing or attenuating the expression of DNA or RNA encoding human 5-HT3-C, or the function of human 5-HT3-C protein. Compounds that modulate the expression of DNA or RNA encoding human 5-HT3-C or the function of human 5-HT3-C protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, research tools and diagnostic agents.

Kits containing human 5-HT3-C DNA or RNA, antibodies to human 5-HT3-C, or human 5-HT3-C protein may be prepared. Such kits are used to detect DNA that hybridizes to human 5-HT3-C DNA or to detect the presence of human 5-HT3-C protein or peptide fragments in a sample. Such characterization is useful for a variety of purposes including but not limited to forensic analyses, diagnostic applications, and epidemiological studies.

The DNA molecules, RNA molecules, recombinant protein and antibodies of the present invention may be used to screen and measure levels of human 5-HT3-C DNA, human 5-HT3-C RNA or human 5-HT3-C protein. The recombinant proteins. DNA molecules. RNA molecules and antibodies lend themselves to the formulation of kits suitable for the detection and typing of human 5-HT3-C. Such a kit would comprise a compartmentalized carrier suitable to hold in close confinement at least one container. The carrier would further comprise reagents such as recombinant human 5-HT3-C protein or anti-human 5-HT3-C antibodies suitable for detecting human 5-HT3-C. The carrier may also contain a means for detection such as labeled antigen or enzyme substrates or the like.

Nucleotide sequences that are complementary to the human 5-HT3-C encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other human 5-HT3-C antisense oligonucleotide mimetics. Human 5-HT3-C antisense molecules may be introduced into cells by microinjection, liposome encapsulation or by expression from vectors harboring the antisense sequence. Human 5-HT3-C antisense therapy may be particularly useful for the treatment of diseases where it is beneficial to reduce human 5-HT3-C activity.

Human 5-HT3-C gene therapy may be used to introduce human 5-HT3-C into the cells of target organisms. The human 5-HT3-C gene can be ligated into viral vectors that mediate transfer of the human 5-HT3-C DNA by infection of recipient host cells. Suitable viral vectors include retrovirus, adenovirus, adeno-associated virus, herpes virus, vaccinia virus, poliovirus and the like. Alternatively, human 5-HT3-C DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo human 5-HT3-C gene therapy. Human 5-HT3-C gene therapy may be particularly useful for the treatment of diseases where it is beneficial to elevate human 5-HT3-C activity. Two examples of therapeutic strategies could be to as follows: (A) introduction of 5-HT3-C into a tissue that does not naturally express the subunit with the purpose of decreasing the 5-HT3 receptor response in asthma, inflammation and vagal nerve terminals to block 5-HT effects; or (B) Antisense strategies to decrease 5-HT3-C levels in tissue that naturally express the subunit with the purpose to elevate responsiveness of the 5-HT3 receptor complex.

Pharmaceutically useful compositions comprising human 5-HT3-C DNA, human 5-HT3-C RNA, or human 5-HT3-C protein, or modulators of human 5-HT3-C receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of human 5-HT3-C—related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the human 5-HT3-C receptor or its activity while minimizing any potential toxicity. In addition, co-administration or sequential administration of other agents may be desirable.

The present invention also has the objective of providing suitable topical oral, systemic and parenteral pharmaceutical formulations for use in the novel methods of treatment of the present invention. The compositions containing compounds or modulators identified according to this invention as the active ingredient for use in the modulation of human 5-HT3-C receptors can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a serotonin 5-HT3-A/5-HT3-C receptor modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the human 5-HT3-C receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules; elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methylcellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, e.g., alcohols, aloe vera gel, allantoin, glycerine, vitamin A and E olis, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenyl, polyhydroxy-ethylaspartamidephenyl, or polyethyl-eneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cottonseed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Cloning of p5HT3CR

Rapid Amplification of cDNA Ends (RACE) Method of Human 5-HT3-C cDNA

The RACE method of cDNA cloning was performed using a Marathon™ cDNA amplification kit (Clonetech, Palo Alto, Calif.) essentially as described by the manufacture's instructions. The primary PCR reaction was conducted using a human lung cDNA (cDNA synthesized using 2 μg of human lung mRNA (Clontech) and random hexamers (Superscript cDNA synthesis kit—Life Technologies), being amplified using an AP1 primer (Clonetech) and two unique internal primers). The two primers for RACE were identified as a nucleotide fragment with partial identity to the 5-HT3-A receptor, indicating a punitive new receptor subtype or subunit. The primers were synthesized and have the following sequences:

(SEQ.ID.NO.1)
CHNL 86-6 5' GTAGAAGCTGAGGCCATCAATGGCAAC 3',
and (SEQ.ID.NO.2)
CHNL 86-4 5' CTGGTCACCCTCATTGGCTTATCATAC 3'.

Following the primary PCR, a secondary PCR reaction was conducted using a nested PCR primer and the AP1 primer to amplify the PCR product of the primary reaction. The nested PCR primer was synthesized and has the following sequence:

(SEQ.ID.NO.3)
CHNL 86-2 5' ACTGACAGTGAGGCAGAGGAGGGCA 3'.

The PCR product of the secondary reaction was hybridized with a $^{32}P$ oligonucleotide and run on a 1% agarose gel to ensure that the RACE method yielded a specific cDNA product. The labeled oligonucleotide has the following sequence:

(SEQ.ID.NO.4)
CHNL 86-1 5' CCTGGTGAATCCCCAGAGAAGAGTG 3'.

The PCR product was cloned into pGemHE and pCDNA3.1/Zeo vectors and sequenced to identify the complete cDNA sequence of the subunit.

EXAMPLE 2

Cloning of 5-HT3-C cDNA into a Mammalian Expression Vector

The 5-HT3-C cDNAs (collectively referred to as p5HT3CR) were cloned into the mammalian expression vector pcDNA3.1zeo(+) (InVitrogen). The 5-HT3-C cDNA clone was isolated from a human lung cDNA library. The full-length cDNA was used as the template for PCR using specific primers with BamHI (5'AAC GTT GAA TTC GCC ACC ATG TTG TCA AGT GTA ATG GCT CCC CTG TGG GCC3') [SEQ.ID.NO. 7] and HindIII (5'AAC GTT AAG CTT TCT TAA GTG CCA GCA CAA TTA CTT GAA G 3') [SEQ.ID.NO. 8] sites for cloning. The PCR product was purified on a column (Wizard PCR DNA purification kit from Promega) and digested with NheI and NotI (NEB) to create cohesive ends. The product was purified by a low melting agarose gel electrophoresis. The pcDNA3.1zeo(+) vector was digested with NheI and NotI enzymes and subsequently purified on a low melt agarose gel. The linear vector was used to ligate to the 5-HT3-C cDNA inserts. Recombinants were isolated and designated 5-HT3-C. Cell lines (in HEK293) were transfected to stably express 5-HT3-C (5-HT3-C/HEK). These recombinant cell lines can be used to transiently transfect other receptors such as 5-HT3-A as well as to transfect the human 5-HT3-A receptor in a pCIneo vector (using EcoRI and XbaI cloning sites) (5-HT3-A/HEK293 cells) by electroporation to stably express human 5-HT3-A or other receptor subunit together with 5-HT3-C. Stable 5-HT3-C/HEK cell clones were selected by growth in the presence of zeocin; double transfectants are selected by growth in the presence of G418 and zeocin. Single G418/zeocin resistant clones are isolated and shown to contain the intact 5-HT3-C gene. Clones containing the human 5-HT3-C cDNAs were analyzed for p5HT3CR expression by measuring membrane potential changes using Fluo-4 and DiBAC$_4$(3) in response to serotonin, and about 300 other ligands (see Example 6). Responses were compared to those obtained from untransfected HEK293 cells.

Cells stably expressing human 5-HT3-C together with human 5-HT3-A are used to test for expression of human 5-HT3-C and for functional activity. These cells are used to identify and examine other compounds for their ability to modulate, inhibit or activate the human 5-HT3-C. Other cells expressing both 5HT3-A and 5-HT3-C subunits can be used to identify and examine other compounds for their ability to modulate, inhibit or activate the human 5-HT3-C.

Cassettes containing the human 5-HT3-C cDNA in the positive orientation with respect to the promoter are ligated into appropriate restriction sites 3' of the promoter and identified by restriction site mapping and/or sequencing. These DNA expression vectors are introduced into fibroblastic host cells for example HEK293 by standard methods including but not limited to electroporation, or chemical procedures (cationic liposomes, DEAE dextran, calcium phosphate).

All of the vectors used for mammalian transient expression can be used to establish stable cell lines expressing the human 5-HT3-C. Unaltered human 5-HT3-C constructs cloned into expression vectors are expected to program host cells to make human 5-HT3-C protein. The transfection host cells include, but are not limited to, HEK293, CV-1-P [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing the human 5-HT3-C cDNA with a drug selection plasmid including, but not limited to G418, zeocin, aminoglycoside phosphotransferase; hygromycin, hygromycin-B phosphotransferase; APRT, xanthine-guanine phosphoribosyl-transferase, will allow for the selection of stably transfected clones. Levels of the human 5-HT3-C are quantitated by the assays described herein.

The human 5-HT3-C cDNA constructs are also ligated into vectors containing amplifiable drug-resistance markers for the production of mammalian cell clones synthesizing the highest possible levels of the human 5-HT3-C. Following introduction of these constructs into cells, clones containing the plasmid are selected with the appropriate agent, and isolation of an over-expressing clone with a high copy number of plasmids is accomplished by selection in increasing doses of the agent.

The expression of recombinant human 5-HT3-C is achieved by transfection of full-length the human 5-HT3-C cDNA into a mammalian host cell.

EXAMPLE 3

Primary Structure of the Human 5-HT3-C Protein

The nucleotide sequences of p5HT3BR revealed single large open reading frame of about 1341 base pairs as shown in FIG. 2. The cDNAs have 5' and 3'-untranslated extensions of about 34 and about 367 nucleotides for p5HT3CR. The first in-frame methionine was designated as the initiation codon for an open reading frame that predicts a human 5-HT3-C protein with an estimated molecular mass ($M_r$) of about 50.2 kDa. The protein contained hydrophobic amino terminal residues with sequences highly predictive of signal cleavage sites that would result in mature proteins initiating at amino acid 28 (SignalP analysis; Henrik Nielsen, Jacob Engelbrecht, Søren Brunak and Gunnar von Heijne: Identification of prokaryotic and eukaryotic signal peptides and prediction of their cleavage sites. *Protein Engineering*, 10, 1–6 (1997)).

The predicted human 5-HT3-C protein was aligned with nucleotide and protein databases and is related to known 5-HT3-A receptors. Approximately 66% of the amino acids in 5-HT3-C were highly conserved, showing at least 39% amino acid identity within the human 5-HT3-A serotonin receptor. The conserved motifs found in this family of receptor, such as the 4 putative transmembrane domains with similar spacing, were also found in the human 5-HT3-C sequence. The identity of the 5-HT3-C receptor with the 5-HT3-A receptor at the nucleotide level was only about 50%. The strongest homology is in the 4 putative transmembrane domains, in particular TM2 and TM3 which are 65 and 62% identical to 5-HT3-A, respectively. The human 5-HT3-C protein contained the conserved cysteine residues found in the conserved cysteine-cysteine loop that may form the agonist-binding site of ligand-gated ion channels (Lambert et al., 1995). There is strong homology to the proposed ligand recognition site in the first N-terminal loop in the murine 5-HT3-A and the nicotinic AChR α7. [xIWxP-DILxxExxD]; only 2 differences in the shown "consensus" in the 5-HT3-C protein are conserved changes. The E106 in the 5-HT3-A (murine) is critical for high affinity 5-HT binding (Boess et al., 1997); E129 is in the homologous position of the 5-HT3-C protein.

Four potential sites of glycosylation (Marshall, 1972) were located at the extracellular amino terminus. Interestingly, there were no potential sites for protein kinase A or C (Woodgett et al., 1986), casein kinase II (Pinna, 1990), or mammary gland casein kinase in the putative cytoplasmic loops.

EXAMPLE 4

Distribution of 5-HT3-C mRNA

The tissue distribution of 5-HT3-C mRNAs was determined by semi-quantitative PCR A primer set specific to 5-HT3-C 5'primer CGTGGAATCCATGGATGTGG [SEQ.ID.NO. 10]; 3'primer TGGCAGGGAGCAAGTCATTC [SEQ.ID.NO.11] was used to complete amplification of a portion of the 5-HT3-C mRNA via PCR using cDNAs templates synthesized from poly (A) RNA (Clontech, Palo Alto, Calif.) which was extracted from various human tissues (tissue types shown in FIG. 6a). To gain increased specificity and sensitivity, an oligonucleotide GTGG-GAGATCACAGACACGTCTCGCAAAGT [SEQ.ID.NO.12] was phosphorylated using $\gamma$-$^{32}$P-ATP with polynucleotide kinase as described by manufacturer (Amersham Pharmacia Biotech, Piscataway, N.J.) and annealed to denatured PCR products and resolved by 6% polyacrylamide gel electrophoresis. The subsequent gel was then dried down and exposed to X-ray film.

As shown in FIG. 6a, PCR-based tissue distribution analysis reveals that the 5-HT3-C mRNA is expressed in human lung, prostrate, bone marrow, small intestine, stomach, uterus, testis, mammary gland, thyroid and less abundantly in amygdala, cerebellum, heart, liver, pancreas, placenta, spinal cord, thymus, adrenal gland, lymph node, salivary gland, substantia nigra and trachea. No detectable transcript was observed in hippocampus, kidney, skeletal muscle, spleen, thalamus, and caudate. cDNA libraries were screened and expression was observed in DRG, small intestine, hypothalamus, cortex, cerebellum and lung libraries. There was no detectable expression in spleen, thalamus, placenta, heart, liver, uterus, pituitary, spinal cord, bone marrow, hippocampus libraries.

Microarray analysis of 5-HT3-C and 5-HT3-A expression revealed some overlap of 5-HT3-B and 5-HT3-A receptor distributions and corroborate the results shown in FIG. 6a. The distribution of 5-HT3-C mRNA was determined using cDNA microarray analysis of cRNA amplified from mRNAs extracted from a variety of tissues and cell types. The methods are as described in Luo et al., 1999 Nature Medicine 5(1):117. As seen in FIG. 6b, 5-HT3-C mRNA, and presumably functional protein, is expressed in many tissues as indicated by a survey analysis of myeloid and solid tissue analysis.

EXAMPLE 5

Characterization of the Function of Protein Encoded by p5HT3CR in *Xenopus oocytes Xenopus laevis* oocytes were prepared and injected using standard methods previously described and known in the art (Fraser et al., 1993). Ovarian lobes from adult female *Xenopus laevis* (Nasco, Fort Atkinson, Wis.) were teased apart, rinsed several times in nominally Ca-free saline containing (in mM): NaCl 82.5, KCl 2.5, $MgCl_2$ 1, HEPES 5, adjusted to pH 7.0 with NaOH (OR-2), and gently shaken in OR-2 containing 0.2% collagenase Type 1 (ICN Biomedicals, Aurora, Ohio) for 2–5 hours. When approximately 50% of the follicular layers were removed, Stage V and VI oocytes were selected and rinsed in media consisting of 75% OR-2 and 25% ND-96. The ND-96 contained (in mM): NaCl 100, KCl 2, $MgCl_2$ 1, $CaCl_2$ 1.8, HEPES 5, Na pyruvate 2.5, gentamicin (50 ug/ml), adjusted to pH 7.0 with NaOH. The extracellular $Ca^{2+}$ was gradually increased and the cells were maintained in ND-96 for 2–24 hours before injection. For in vitro transcription, pGEM HE (Liman et al., 1992) containing human 5-HT3-A (Genbank D49394) or 5-HT3-C cDNA was linearized with NheI and transcribed with T7 RNA polymerase (Stratagene) in the presence of the cap analog m7G(5')ppp(5')G. The synthesized cRNA was purified with a Sephadex G-50 spin column. Oocytes were injected with 50 nl of the human serotonin 5-HT3-A receptor with or without the 5-HT3-C RNA (0.02 and 0.002–0.2 ng each) or other channel or receptor subunit. Control oocytes were injected with 50 nl of water. Oocytes were incubated for 2–14 days in ND-96 before analysis for expression of the human 5-HT3-C. Incubations and collagenase digestion were carried out at room temperature. Injected oocytes were maintained in 48 well cell culture clusters (Costar, Cambridge, Mass.) at 18° C. Whole cell agonist-induced currents were measured 1–14 days after injection with a conventional two-electrode voltage clamp (GeneClamp500, Axon Instruments, Foster City, Calif.) using standard methods previously described and known in the art (Dascal, 1987). The microelectrodes were filled with 3 M KCl, which had resistances of 1 and 2 MΩ. Cells were continuously perfused with ND96 at 10 ml/min at room temperature unless indicated. Membrane voltage was clamped at −70 mV unless indicated.

No response to tested agonists (see below) was detected when oocytes were injected with 5-HT3-C alone or in combination with nicotinic ACh β1, β2, and β3 subunits or with nicotinic ACh α6.

5-HT ($\geq 100$ μM) had no effect in oocytes injected with putative 5-HT3-C subunit alone (n=11 (33.5 ng cRNA/oocyte) and n=2 (3.35 ng). The 5-HT3 receptor agonist 1-PBG had no effect at 100 μM (n=4) and 500 μM (n=3) (oocytes were injected with 33.5 ng 5-HT3-C). No effect was observed for 10 μM (n=5) and 500 μM ACh (n=3), and both 5-HT (10 μM) and ACh (500 μM) applied together, 100 μM DA (n=11), 10 μM histamine (n=4), >30 μM GABA (n=6), 100 M Glycine (n=4) (all oocytes injected with 33.3 ng 5-HT3-C cRNA). Similar results were obtained for oocytes injected with 3.35 ng 5-HT3-C cRNA.

Oocytes injected with only 5-HT3-C cRNA (33.5 ng) or 5-HT3-C together with nicotininc ACh receptor subunits β1, β2 and β3 (0.2–0.25 ng) were insensitive to 30 neuroactive compounds at >100 μM including 5-HT, ACh, histamine, tyramine, tryptamine, tryptophanamide, tryptophan, norepinephrine, octopamine, DA, glutamate, L- and D-aspartate, glycine, GABA, β-alanine, taurine, β-phenylethylamine, 5-hydroxyindolacetic acid, 6-hydroxymelatonin, gamma hydroxybutyrate, cis-4 aminocrotonic acid, agmatine, d-cycloserine, N-acetyl-L-cysteine, acetyl-aspartyl-L-glutamic acid, melatonin, 5-hydroxyindole 2-carboxylic acid, N-acetyl serotonin, and 5-hydroxyindole 3-acetamide (n=5).

Eight days after injection with 5-HT3-C (0.67 ng/oocyte) together with nicotinic ACh receptor a6 subunit (1 ng/oocyte), oocytes were not responsive to 10 μM epibatidine, 500 μM ACh, 10 μM 5-HT, or both ACh and 5-HT together (n=5).

Functional expression of human serotonin 5-HT3 receptor modifier subunit 5-HT3-C together with the human short form of the 5-HT3-A receptor (Genbank accession # D49394) in *Xenopus oocytes* is shown in FIGS. 4 and 5. The inward current through 5-HT3-A homomeric receptors during the continued presence of 10 μM 5-HT is shown in FIG. 4 (top right panel). Agonist was applied during the time indicated by the horizontal bar above the record. In oocytes co-injected with 2-fold more 5-HT3-C cRNA (0.67 ng), the peak response to 5-HT was dramatically decreased (to about 10% of control). As a positive control for translation and surface expression, all oocytes were co-injected with a Shaker potassium channel N-terminal deletion mutant that lacks fast inactivation. In the same oocytes revealing decreased 5-HT responses, families of voltage-activated currents mediated by a Shaker N-terminal deletion mutant were unaffected by co-injection with 5-HT3-C (top panel, bottom traces). Oocytes were continuously perfused with $Ba^{2+}$ containing ND96 at a rate of 10 ml/min at room temperature. Time scale bar: 25 sec. Similar results were obtained in experiments in which oocytes were bathed in $Ca^{2+}$ containing ND96.

The specificity of the 5-HT3-C effect was further investigated by co-injection with the nicotinic receptors α3β4 and α4β2 in oocytes. Co-injection of the 5-HT3-C cRNA (3.35 ng) had no effect on peak currents through nicotinic ACh α3β4 receptors activated by 10 μM epibatidine (FIG. 4, bottom panel and FIG. 5). Peak currents were −6.93+/−1.45 nA (n=11) and 6.49+/−0.69 nA (n=7) for α3β4 nACh receptors and α3β4 receptors together with 5-HT3-C, respectively. These results were obtained from 3 separate experiments. 5-HT3-C had no effect on the time between 80% rise to peak and 20% decline from peak (t80), the time to peak, and the degree of desensitization to a second epibatidine stimulus. Thus, co-injection of 5-HT3-C had a specific effect on 5-HT3-A(short) receptor function and did not have a general detrimental effect on translation since voltage-activated Shaker potassium currents and nicotinic ACh α3β4 and α4β2 receptor responses were no different in the presence of 5-HT3-C.

5-HT3-C co-expression dose-dependently decreased the responsiveness of oocytes expressing 5-HT3-A(short). Oocytes injected with both 5-HT3-A (0.33 ng) and 5-HT3-C (3.35 ng) cRNA were essentially insensitive to 5-HT (5-HT3-C: 5-HT3-A(short) was 10:1). Responses to 10 LM 5-HT were −3.89+/−0.76 nA (n=6) in 5-HT3-A(short)-injected oocytes and −0.010+/−0.008 nA (n=6) in oocytes injected with both 5-HT3-A(short) and 5-HT3-C (p<0.005; Student's t test). Oocytes injected with 5-HT3-C and 5-HT3-A(short) at a ratio of 2:1 (FIGS. 4,5) revealed peak currents to 5-HT of −0.028+/−0.007 nA (n=20) compared to −1.65+/−0.42 nA (n=19) for 5-HT3-A(short)-expressing oocytes (p 20<0.001). Interestingly, at a 1.8×fold 5-HT3-C to 5-HT3-A cRNA concentration, the 5-HT response was diminished about 20% (n=3), and oocytes injected with a 1:1 ratio revealed little effect of 5-HT3-C (n=6), suggesting that if heteromers of 5-HT3-A and 5-HT3-C are formed, more than half of the receptor complex must consist of 5-HT3-C to decrease receptor function.

The pharmacological profile of 5-HT3-A receptors was studied in oocytes co-injected with both 5-HT3-A and 5-HT3-C. The 5-HT3 receptor agonists 1-PBG, DA, and N-ω-methyl-5-HT (100 µM), as well as tryptamine (100 µM) were bath applied to oocytes co-injected with 5-HT3-C and 5-HT3-A (5:1 ratio). The ratio of peak responses to 10 and 100 µM 1-PBG and 100 µM and 1 mM DA were similar to that observed for 5-HT3-A homomers indicating 5-HT3-C had no dramatic effect on the dose response to these agonists. The kinetics of currents induced by all tested agonists were similar with or without 5-HT3-C.

5-HT3-C modulation of channel properties were observed in salines deplete of $Ca^{2+}$, and at membrane potentials near the chloride equilibrium potential.

Oocytes co-injected with the long form of human 5-HT3-A (Genbank Accession # AJ003078), which had no functional expression when injected alone, together with 5-HT3-C were insensitive to application of 10 µM 5-HT (n=2) or 100 µM 1-PBG (n=2).

Oocytes co-injected with both 5-HT3-B (3.3 ng/oocyte) and 5-HT3-C (3.35 ng/oocyte) were unresponsive to 10 µM 5-HT (n=2 of 2), 10 µM epibatidine (n=4 of 4), 100 µM N-ω-methyl-5-HT (n=3 of 3), a mixture of γ-hydroxybutyrate (0.3 mM), β-phenylethylamine (0.3 mM) and dopamine (0.5 mM) (n=2 of 2), a mixture of 10 µM mCPBG, 100 µM 1-PBG, 100 µM tryptamine, and 100 µM tyramine (n=3 of 3), 10 µM IL-1 (n=4 of 4), and 1 µM gastrin (n=3 of 3).

5-HT3-C (0.85 ng/oocyte) co-injection with 5-HT3A-short (0.45 ng/oocyte) together with 5-HT3-B (3.3 ng/oocyte) revealed no effect in 5-HT3 receptor agonist response and time course.

EXAMPLE 6

Characterization of the Human 5-HT3-C in a Mammalian Cell Line

Human HEK293 cells stably expressing human 5-HT3-C were constructed. Initially, transfections of 5-HT3-C in pCINeo (EcoRI/XbaI) were attempted with Transfectamine (Promega) and Effectene (Stratagene) but cells died quickly after transfection, even without selection in G418 (500 µg/ml). In order to maintain the transfected cells, cells were plated on a feeder cell layer. Since Zeocin eliminates untransfected HEK293 cells more rapidly and efficiently than G418, 5-HT3-C was cloned into the pcDNA3.1/Zeo vector (EcoRI/NotI sites).

About $5 \times 10^6$ untransfected HEK 293 cells in 10 ml media was irradiated in CS 126 machine for 20 minutes. One million irradiated cells were plated together with about 1 million transfected cells (5-HT3-C/pCDNA 3.1 Zeocin/HEK 293) on 100 mm dishes. The FBS media content was increased from 10% to 20% to aid the survival of transfected cells, and zeocin (200 µg/ml) selection was begun one day later. After two months of 1:5 splits, a pool of stably transfected cells was obtained.

Poly(A)+ mRNA was isolated from the pool, cDNA made by reverse transcription, and PCR with gene-specific primers for 5-HT3-C was performed. An internal probe labeled with 32P-γ-ATP was used to confirm that the detected PCR band contained the specific 5-HT3-C sequence. This indicated expression of 5-HT3-C mRNA in cells contained in the pool.

Cells from the pool were then plated onto 96-well plates (Biocoat, poly-D-lysine coated black/clear plate, Becton Dickinson part # 354640) and grown to confluence for three days. In experiments measuring intracellular Ca2+ levels, wells were rinsed with F12/DMEM, then incubated in Fluo-4 (2 µM) with Pluronic acid (20%, 40 µl used in 20 ml total volume) for 1 hour at room temperature. Plates were assayed using the FLIPR (Molecular Devices, FL-101). Cells were challenged with agonists (at 3-fold concentration in 40 µl added to 80 µl at a velocity of 50 µl/sec). In experiments measuring membrane potential changes with the slow voltage sensitive dye $DiBAC_4(3)$, cells were washed three times with 2K/2Ca buffer [in mM: 2 KCl, 128 NaCl, 1 $MgCl_2$, 2 $Ca_2Cl$, 15 dextrose, 20 HEPES] containing 5 µM $DiBAC_4(3)$. Drugs (20 µl) were added to wells containing 180 µl of 2K/2Ca buffer containing 5 µM $DiBAC_4(3)$. Pipette tips were pre-soaked for 2 min in 2K/2Ca buffer containing 10 µM $DiBAC_4(3)$ prior to addition of solutions to cell plates. $DiBAC_4(3)$ signals were measured on the FLIPR after addition of ligands in $DiBAC_4(3)$ solution at a rate of 50 µl/sec.

Stably transfected cells (5-HT3-C/HEK) were tested for their sensitivity to nearly 300 agonists using the FLIPR system using the $Ca^{2+}$ and voltage sensitive dyes Fluo-4 and $DiBAC_4(3)$ (Molecular Probes, Eugene Oreg.) to measure changes in the membrane potential. No response was observed when cells were maintained at their resting potential; as control for the DIBAC, cells stably expressing 5-HT3-A receptors responded to 5-HT and other 5-HT3 receptor specific ligands with a fast transient depolarization (increase in fluorescence).

EXAMPLE 7

Binding Assay on Human 5-HT3-C and 5-HT3-A Co-Transfected Mammalian Cells.

HEK293 cells stably expressing 5-HT3-C receptor with or without transient expression of human 5-HT3-A can be used in $^3$H-[mCPBG] or $^3$H-[Y25130 or MDL 72222] binding assays. Equilibrium ligand binding assays can be performed using conventional procedures (Lummis and Baker, 1997; Lummis et al., 1993). Specific $^3$H-[mCPBG] or $^3$H-[Y25130 or MDL 72222] binding is observed in membrane preparations from h5-HT3 receptor and human 5-HT3-C transfected cells. Oocytes expressing 5-HT3-A and human 5-HT3-C can be used to measure the affinity of binding of other compounds and their ability to displace $^3$H-[mCPBG] or $^3$H-[Y25130 or MDL 72222] binding.

EXAMPLE 8

Cloning of the Human 5-HT3-C cDNA into *E. coli* Expression Vectors

Recombinant human 5-HT3-C is produced in *E. coli* following the transfer of the expression cassette into *E. coli* expression vectors, including but not limited to, the pET series (Novagen). The pET vectors place human 5-HT3-C expression under control of the tightly regulated bacteriophage T7 promoter. Following transfer of this construct into an *E. coli* host that contains a chromosomal copy of the T7 RNA polymerase gene driven by the inducible lac promoter, expression of human 5-HT3-C is induced when an appropriate lac substrate (IPTG) is added to the culture. The levels of expressed human 5-HT3-C are determined by the assays described herein.

The cDNA encoding the entire open reading frame for human 5-HT3-C is inserted into the NdeI site of pET[16]11a. Constructs in the positive orientation are identified by sequence analysis and used to transform the expression host strain BL21. Transformants are then used to inoculate cultures for the production of human 5-HT3-C protein. Cultures may be grown in M9 or ZB media, whose formulation is known to those skilled in the art. After growth to an $OD_{600}$ to approximately 1.5, expression of human 5-HT3-C is induced with 1 mM IPTG for 3 hours at 37° C.

EXAMPLE 9

Cloning of Human 5-HT3-C cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing human 5-HT3-C cDNA is produced by the following standard methods (InVitrogen Maxbac Manual): the human 5-HT3-C cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells and recombinant pBlueBac viruses are identified on the basis of B-galactosidase expression (Summers, M. D. and Smith, G. E., Texas Agriculture Exp. Station Bulletin No. 1555). Following plaque purification, human 5-HT3-C expression is measured by the assays described herein.

The cDNA encoding the entire open reading frame for human 5-HT3-C is inserted into the BamHI site of pBlue-BacII. Constructs in the positive orientation are identified by sequence analysis and used to transfect Sf9 cells in the presence of linear AcNPV mild type DNA.

Authentic, active human 5-HT3-C is found in the cytoplasm of infected cells. Active human 5-HT3-C is extracted from infected cells by hypotonic or detergent lysis.

EXAMPLE 10

Cloning of Human 5-HT3-C cDNA into a Yeast Expression Vector

Recombinant human 5-HT3-C is produced in the yeast *S. cerevisiae* following the insertion of the optimal human 5-HT3-C cDNA cistron into expression vectors designed to direct the intracellular or extracellular expression of heterologous proteins. In the case of intracellular expression, vectors such as EmBLyex4 or the like are ligated to the human 5-HT3-C cistron [Rinas U. et al., Biotechnology 8: 543–545 (1990); Horowitz B. et al., J. Biol. Chem. 265: 4189-4192 (1989)]. For extracellular expression, the human 5-HT3-C cistron is ligated into yeast expression vectors which fuse a secretion signal (a yeast or mammalian peptide) to the NH2 terminus of the human 5-HT3-C protein [Jacobson, M. A., Gene 85: 511–516 (1989); Riett L. and BellonN. Biochem. 28: 2941–2949 (1989)].

These vectors include, but are not limited to pAVE1>6, which fuses the human serum albumin signal to the expressed cDNA [Steep O. Biotechnology 8: 42-46 (1990)], and the vector pL8PL which fuses the human lysozyme signal to the expressed cDNA [Yamamoto, Y., Biochem. 28: 2728–2732)]. In addition, human 5-HT3-C is expressed in yeast as a fusion protein conjugated to ubiquitin utilizing the vector pVEP [Ecker, D. J., J. Biol. Chem. 264: 7715–7719 (1989), Sabin, E. A., Biotechnology 7: 705–709 (1989), McDonnell D. P., Mol. Cell Biol. 9: 5517–5523 (1989)]. The levels of expressed human 5-HT3-C are determined by the assays described herein.

EXAMPLE 11

Purification of Recombinant human 5-HT3-C

Recombinantly produced human 5-HT3-C may be purified by antibody affinity chromatography.

Human 5-HT3-C antibody affinity columns are made by adding the anti-human 5-HT3-C antibodies to Affigel-10 (Bio-Rad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized human 5-HT3-C are slowly passed through the column. The column is then washed with phosphate-buffered saline together with detergents until the optical density (A280) falls to background, then the protein is eluted with 0.23 M glycine-HCl (pH 2.6) together with detergents. The purified human 5-HT3-C protein is then dialyzed against phosphate buffered saline.

REFERENCES

Barnard, E. A. (1996). The transmitter-gated channels: a range of receptor types and structures. Trends Pharmacol. Sci. 17, 305–309.

Belelli, D., Balcarek, J. M., Hope, A. G., Peters, J. A., Lambert, J. J., and

Blackburn, T. P. (1995). Cloning and functional expression of a human 5-hydroxytryptamine type 3As receptor subunit. Mol. Pharmacol. 48, 1054–62.

Boess, F. G., Steward, L. J., Steele, J. A., Liu, D., Reid, J., Glencorse, T. A., and Martin, I. L. (1997). Analysis of the ligand binding site of the 5-HT3 receptor using site directed mutagenesis: importance of glutamate 106. Neuropharmacology 36, 637–647.

Bufton, K. E., Steward, L. J., Barber, P. C., and Barnes, N. M. (1993). Distribution and characterization of the [3H] granisetron-labeled 5-HT3 receptor in the human forebrain. Neuropharmacology 32, 1325–31.

Dascal, N. (1987). The use of *Xenopus* oocytes for the study of ion channels. CRC Critical Reviews in Biochemistry 22, 317–387.

Davies, P. A., Pistis, M., Hanna, M. C., Peters, J. A., Lambert, J. J., Hales, T. G., and Kirkness, E. F. (1999). The 5-HT3B subunit is a major determinant of serotonin-receptor function. Nature (London) 397, 359–363.

Derkach, V., Surprenant, A., and North, R. A. (1989). 5-HT3 receptors are membrane ion channels. Nature (London) 339, 706–9.

Fletcher, S., and Barnes, N. M. (1998). Desperately seeking subunits: are native 5-HT3 receptors really homomeric complexes? Trends Pharmacol. Sci. 19, 212–215.

Fletcher, S., and Barnes, N. M. (1997). Purification of 5-hydroxytyptamine3 receptors from porcine brain. Br. J. Pharmacol. 122, 655–662.

Fletcher, S., Lindstrom, J. M., Mckeman, R. M., and Barnes, N. M. (1998). Evidence that porcine native 5-HT3 receptors do not contain nicotinic acetylcholine receptor subunits. Neuropharmacology 37, 397–399.

Fozard, J. R. (1984). Neuronal 5-HT receptors in the periphery. Neuropharmacology 23, 1473–86.

Fraser, S. P., Moon, C., and Djamgoz, M. B. A. (1993). Electrophysiology of Xenopus oocytes: An expression system in molecular neurobiology. In Electrophysiology, D. Wallis, ed.: IRL, Oxford, UK), pp. 65–86.

Furutani, M., Trudeau, M. C., Hagiwara, N., Seki, A., Gong, Q., Zhou, Z., Imamura, S.-i., Nagashima, H., Kasanuki, H., Takao, A., Momma, K., January, C. T., Robertson, G. A., and Matsuoka, R. (1999). Novel mechanism associated with an inherited cardiac arrhythmia: Defective protein trafficking by the mutant HERG (G601 S) potassium channel. Circulation 99, 2290–2294.

Gralla, R. J. (1998). Antiemetic therapy. Semin. Oncol. 25, 577–583.

Greenshaw, A. J., and Silverstone, P. H. (1997). The non-antiemetic uses of serotonin 5-HT3 receptor antagonists: clinical pharmacology and therapeutic applications. Drugs 53, 20–39.

Gurley, D. A., and Lanthom, T. H. (1998). Nicotinic agonists competitively antagonize serotonin at mouse 5-HT3 receptors expressed in Xenopus oocytes. Neurosci. Lett. 247, 107–110.

Hamill, O., Marty, A., Neher, E., Sakmann, B., and Sigworth, F. (1981). Improved patch-clamp techniques for high-resolution current recording from cells and cell-free membrane patches. Pflugers Archives 391, 85–100.

Hugnot, J.-P., Salinas, M., Lesage, F., Guillemare, E., de Weille, J., Heurteaux, C., Mattei, M.-G., and Lazdunski, M. (1996). Kv8.1, a new neuronal potassium channel subunit with specific inhibitory properties towards Shab and Shaw channels. Embo J. 15, 3322–3331.

Jan, L. Y., and Jan, Y. N. (1997). Voltage-gated and inwardly rectifying potassium channels. In J. Physiol. (Cambridge, U.K), pp. 267–282.

Julius, D. (1996). Molecular analysis of serotonin receptor function. Taniguchi Symp. Brain Sci. 19, 151–165.

Kuntzweiler, T. A., Arneric, S. P., and Donnelly-Roberts, D. L. (1998). Rapid assessment of ligand actions with nicotinic acetylcholine receptors using calcium dynamics and FLIPR. Drug Dev. Res. 44, 14–20.

Lambert, J. J., Peters, J. A., and Hope, A. G. (1995). 5-HT3 receptors. In Ligand-Voltage-Gated Ion Channels, R. North, ed.: CRC, Boca Raton, Fla.), pp. 177–211.

Liman, E. R., Tytgat, J., and Hess, P. (1992). Subunit stoichiometry of a mammalian potassium channel determined by construction of multimeric cDNAs. Neuron 9, 861–71.

Lummis, S. C. R., and Baker, J. (1997). Radioligand binding and photoaffinity labeling studies show a direct interaction of phenothiazines at 5-HT3 receptors. Neuropharmacology 36, 665–670.

Lummis, S. C. R., and Martin, I. L. (1992). Solubilization, purification, and functional reconstitution of 5-hydroxytryptamine3 receptors from NIE-115 neuroblastoma cells. Mol. Pharmacol. 41, 18–23.

Lummis, S. C. R., Sepulveda, M. I., Kilpatrick, G. J., and Baker, J. (1993). Characterization of [3H]meta-chlorophenylbiguanide binding to 5-HT3 receptors in N1E-115 neuroblastoma cells. Eur. J. Pharmacol. 243, 7–11.

Maricq, A. V., Peterson, A. S., Brake, A. J., Myers, R. M., and Julius, D. (1991). Primary structure and functional expression of the 5HT3 receptor, a serotonin-gated ion channel. Science (Washington, D.C., 1883-) 254, 432–7.

Mathur, R., Zhou, J., Babila, T., and Koren, G. (1999). Ile-177 and Ser-180 in the SI segment are critically important in Kv1 channel function. J. Biol. Chem. 274, 11487–11493.

Miller, K., Weisberg, E., Fletcher, P. W., and Teitler, M. (1992). Membrane-bound and solubilized brain 5HT3 receptors: improved radioligand binding assays using bovine area postrema or rat cortex and the radioligands 3H-GR65630, 3H-BRL43694, and 3H-LY278584. Synapse (N.Y.) 11, 58–66.

Miyake, A., Mochizuki, S., Takemoto, Y., and Akuzawa, S. (1995). Molecular cloning of human 5-hydroxytryptamine3 receptor: heterogeneity in distribution and function among species. Mol. Pharmacol. 48, 407–16.

Passani, M. B., and Corradetti, R. (1996). Therapeutic potentials of itasetron (DAU 6215), a novel 5-HT3 receptor antagonist, in the treatment of central nervous system disorders. CNS Drug Rev. 2, 195–213.

Peters, J. A., Malone, H. M., and Lambert, J. J. (1992). Recent advances in the electrophysiological characterization of 5-HT3 receptors. Trends Pharmacol. Sci. 13, 391–7.

Salinas, M., de Weille, J., Guillemare, E., Lazdunski, M., and Hugnot, J.-P. (1997). Modes of regulation of Shab $K^+$ channel activity by the Kv8.1 subunit. J. Biol. Chem. 272, 8774–8780.

Salinas, M., Duprat, F., Heurteaux, C., Hugnot, J.-P., and Lazdunski, M. (1997). New modulatory a subunits for mammalian Shab $K^+$ channels. J. Biol. Chem. 272, 24371–24379.

Shalaby, F. Y., Levesque, P. C., Yang, W.-P., Little, W. A., Conder, M. L., Jenkins-West, T., and Blanar, M. A. (1997). Dominant-negative KvLQT1 mutations underlie the LQT1 form of long QT syndrome. Circulation 96, 1733–1736.

Shuck, M. E., Piser, T. M., Bock, J. H., Slightom, J. L., Lee, K. S., and Bienkowski, M. J. (1997). Cloning and characterization of two $K^+$ inward rectifier (Kir) 1.1 potassium channel homologs from human kidney (Kir1.2 and Kir1.3). J. Biol. Chem. 272, 586–593.

Steward, L. J., West, K. E., Kilpatrick, G. J., and Barnes, N. M. (1993). Labeling of 5-HT3 receptor recognition sites in the rat brain using the agonist radioligand [3H]meta-chlorophenylbiguanide. Eur. J. Pharmacol. 243, 13–18.

Stocker, M., Hellwig, M., and Kerschensteiner, D. (1999). Subunit assembly and domain analysis of electrically silent $K^+$ channel a-subunits of the rat Kv9 subfamily. J. Neurochem. 72, 1725–1734.

Sugita, S., Shen, K. Z., and North, R. A. (1992). 5-Hydroxytryptamine is a fast excitatory transmitter at 5-HT3 receptors in rat amygdala Neuron 8, 199–203.

Turton, S., Gillard, N. P., Stephenson, F. A., and McKernan, R M. (1993). Antibodies against the 5-HT3-A receptor identify a 54 kDa protein affinity-purified from NCB20 cells. Mol. Neuropharmacol. 3, 167–71.

Van Hooft, J. A., and Vijverberg, H. P. M. (1995). Phosphorylation controls conductance of 5-HT3 receptor ligand-gated ion channels. Recept. Channels 3, 7–12.

Waeber, C., Schoeffter, P., Hoyer, D., and Palacios, J. (1989). 5-HT3 receptors in the human brain-autoradiographic visualisation using [3H]ICS 205–930. Neuroscience 31, 393.

Yakel, J. L., Shao, X. M., and Jackson, M. B. (1991). Activation and densensitization of the 5-HT3 receptor in a rat glioma .times. mouse neuroblastoma hybrid cell. J. Physiol. (London) 436, 293–308.

Zerr, P., Adelman, J. P., and Maylie, J. (1998). Episodic ataxia mutations in Kv1.1 alter potassium channel function by dominant negative effects or haploinsufficiency. J. Neurosci. 18, 2842–2848

What is claimed is:

1. An isolated and purified human 5-HT3-C protein, wherein said protein comprises the amino acid sequence set forth in SEQ ID NO: 9.

2. An isolated and purified human 5-HT3-C protein consisting of the amino acid sequence set forth in SEQ ID NO: 9.

* * * * *

```
                            SEQUENCE LISTING

<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 1
gtagaagctg agggcatcaa tggcaac                                         27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 2
ctggtcaccc tcattggctt atcatac                                         27

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Nested PCR
      primer

<400> SEQUENCE: 3
actgacagtg aggcagagga gggca                                           25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
cctggtgaat ccccagagaa gagtc                                           25

<210> SEQ ID NO 5
<211> LENGTH: 1745
<212> TYPE: DNA
<213> ORGANISM: Homo sapiens

<400> SEQUENCE: 5
tggtgaatcc ccagagaaga gtccagaaag aagaatggaa ggagggtggc ctgcaaggca     60
gagtgccctc ctctgcctca ctgtcagtct tctgcttcaa ggaagaggcg acgcttttac    120
catcaattgc tcaggctttg accagcatgg ggttgaccct gctgtcttcc aagcagtgtt    180
```

-continued

```
tgacagaaag gccttccgtc cattcaccaa ctacagcatc cctacccgtg tcaacatctc      240
cttcaccctg tctgccatcc tgggagtgga tgcacagctc cagctgctga catcattcct      300
gtggatggat ttggtatggg acaatccttt cattaattgg aacccaaaag agtgtgttgg      360
catcaataaa ctcacagtat tagctgaaaa cctgtggctc ccagacatct tcatcgtgga      420
atccatggat gtggatcaga cgccttccgg tctcactgcc tatatcagca gtgaaggtcg      480
aattaagtat gataagccaa tgagggtgac cagcatctgt aaactggaca tcttctactt      540 ccctttgac caacagaact gtaccttcac cttcagttct ttcctctaca cagtggacag       600
catgctgctg ggcatggaca aggaggtgtg ggagatcaca gacacgtctc gcaaagtcat      660
ccaaacccag ggggagtggg agctcttggg catcaacaag gccaccccaa agatgtccat      720
gggcaacaac ctatatgacc agatcatgtt ttatgtggcc atcaggcgca ggccaagcct      780
ctacatcata aacctgctgg tgcccagtag ctttctggtt gccattgatg ccctcagctt      840
ctacctgcca gcagagagcg agaatcgtgc cccattcaag ataacacttc tgctgggcta      900
caacgtcttc ctgctcatga tgaatgactt gctccctgcc agtggcaccc ccctcatcag      960
tgtctacttc gccctgtgcc tgtccctgat ggtggtcagc ctgctggaga ccgtcttcat     1020
tacctacctg ctgcacgtgg ccaccaccca gccccaccc atgcctaggt ggcttcactc      1080
cctgctgctc cactgcacca gcccagggag atgctgtccc actgcgcccc agaagggaaa    1140
taagggcctg ggtctcaccc tcacccacct gcctggccca aggagccggg ggagttagc      1200 agggaagaag ctgggaccca gagagaccga gccagatggg ggctcagcat ggacaaagac    1260
ccagctaatg gagctgtggg tgcagttcag ccacgcgatg gacaccctgc tcttccgcct    1320
ctacctgctc ttcatggcct cctccatcct tactgtcatt gtcctctgga acacctaggc    1380
agacatcccc cctctctggc aaacaacagc ttggagtttc tgctggtctt gggccagccg    1440 gactcattt cctaatctta gccacttatc cccagtgact accatgtccc cttctaaatt    1500
ccaaagaatc caacgcagca ctagcaagca ggttcaggac agccctggac gatttcccga    1560
ccgctgctca gggtggtcat tcctgctcac cctcagtttc cctgaggtac cacctaactc    1620
ctcactccct gatcaatgga agttcaggtc agtggagtct ttccttgatt gatcaccca     1680 ataacaact tttcagggaa aaaaaaaaa aaaaaaaaa aaaaaaaaaa aaaaaaaaaa       1740
aaaaa                                                                1745
```

```
<210> SEQ ID NO 6
<211> LENGTH: 1344
<212> TYPE: DNA
<213> ORGANISM: Homo sapiens

<400> SEQUENCE: 6
```

```
atggaaggag ggtggcctgc aaggcagagt gccctcctct gcctcactgt cagtcttctg       60
cttcaaggaa gaggcgacgc ttttaccatc aattgctcag gctttgacca gcatggggtt      120
gaccctgctg tcttccaagc agtgtttgac agaaaggcct tccgtccatt caccaactac     180
agcatcccta cccgtgtcaa catctccttc accctgtctg ccatcctggg agtggatgca     240
cagctccagc tgctgacatc attcctgtgg atggatttgg tatgggacaa tcctttcatt    300
aattggaacc caaaagagtg tgttggcatc aataaactca gtattagc tgaaaacctg      360 tggctcccag acatcttcat cgtggaatcc atggatgtgg atcagacgcc ttccggtctc   420
actgcctata tcagcagtga aggtcgaatt aagtatgata agccaatgag ggtgaccagc    480
```

```
atctgtaacc tggacatctt ctacttccct tttgaccaac agaactgtac cttcaccttc      540
agttctttcc tctacacagt ggacagcatg ctgctgggca tggacaagga ggtgtgggag      600
atcacagaca cgtctcgcaa agtcatccaa acccagggg agtgggagct cttgggcatc       660
aacaaggcca ccccaaagat gtccatgggc aacaacctat atgaccagat catgttttat     720
gtggccatca ggcgcaggcc aagcctctac atcataaacc tgctggtgcc cagtagcttt     780
ctggttgcca ttgatgccct cagcttctac ctgccagcag agagcgagaa tcgtgcccca     840
ttcaagataa cacttctgct gggctacaac gtcttcctgc tcatgatgaa tgacttgctc     900
cctgccagtg gcaccccct catcagtgtc tacttcgccc tgtgcctgtc cctgatggtg      960
gtcagcctgc tggagaccgt cttcattacc tacctgctgc acgtggccac cacccagccc    1020
ccacccatgc ctaggtggct tcactccctg ctgctccact gcaccagccc agggagatgc    1080
tgtcccactg cgccccagaa gggaaataag ggcctgggtc tcaccctcac ccacctgcct    1140
ggcccaaagg agccggggga gttagcaggg aagaagctgg acccagaga gaccgagcca      1200 gatgggggct caggatggac aaagacccag ctaatggagc tgtgggtgca gttcagccac    1260
gcgatggaca ccctgctctt ccgcctctac ctgctcttca tggcctcctc catccttact    1320
gtcattgtcc tctggaacac ctag                                            1344
```

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: cloning oligonucleotide for mammalian vector

<400> SEQUENCE: 7

```
aacgttgaat tcgccaccat gttgtcaagt gtaatggctc ccctgtgggc c              51
```

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: cloning oligonucleotide for mammalian vector

<400> SEQUENCE: 8

```
aacgttaagc tttcttaagt gccagcacaa ttacttgaag                           40
```

<210> SEQ ID NO 9
<211> LENGTH: 447
<212> TYPE: PRT
<213> ORGANISM: Homo sapiens

<400> SEQUENCE: 9

```
Met Glu Gly Gly Trp Pro Ala Arg Gln Ser Ala Leu Leu Cys Leu Thr
 1               5                  10                  15

Val Ser Leu Leu Leu Gln Gly Arg Gly Asp Ala Phe Thr Ile Asn Cys
                20                  25                  30

Ser Gly Phe Asp Gln His Gly Val Asp Pro Ala Val Phe Gln Ala Val
            35                  40                  45

Phe Asp Arg Lys Ala Phe Arg Pro Phe Thr Asn Tyr Ser Ile Pro Thr
        50                  55                  60

Arg Val Asn Ile Ser Phe Thr Leu Ser Ala Ile Leu Gly Val Asp Ala
 65                  70                  75                  80
```

```
Gln Leu Gln Leu Leu Thr Ser Phe Leu Trp Met Asp Leu Val Trp Asp
                85                  90                  95

Asn Pro Phe Ile Asn Trp Asn Pro Lys Glu Cys Val Gly Ile Asn Lys
            100                 105                 110

Leu Thr Val Leu Ala Glu Asn Leu Trp Leu Pro Asp Ile Phe Ile Val
        115                 120                 125

Glu Ser Met Asp Val Asp Gln Thr Pro Ser Gly Leu Thr Ala Tyr Ile
    130                 135                 140

Ser Ser Glu Gly Arg Ile Lys Tyr Asp Lys Pro Met Arg Val Thr Ser
145                 150                 155                 160

Ile Cys Asn Leu Asp Ile Phe Tyr Phe Pro Phe Asp Gln Gln Asn Cys
                165                 170                 175

Thr Phe Thr Phe Ser Ser Phe Leu Tyr Thr Val Asp Ser Met Leu Leu
            180                 185                 190

Gly Met Asp Lys Glu Val Trp Glu Ile Thr Asp Thr Ser Arg Lys Val
        195                 200                 205

Ile Gln Thr Gln Gly Glu Trp Glu Leu Leu Gly Ile Asn Lys Ala Thr
    210                 215                 220

Pro Lys Met Ser Met Gly Asn Asn Leu Tyr Asp Gln Ile Met Phe Tyr
225                 230                 235                 240

Val Ala Ile Arg Arg Arg Pro Ser Leu Tyr Ile Ile Asn Leu Leu Val
                245                 250                 255

Pro Ser Ser Phe Leu Val Ala Ile Asp Ala Leu Ser Phe Tyr Leu Pro
            260                 265                 270

Ala Glu Ser Glu Asn Arg Ala Pro Phe Lys Ile Thr Leu Leu Leu Gly
        275                 280                 285

Tyr Asn Val Phe Leu Leu Met Met Asn Asp Leu Leu Pro Ala Ser Gly
    290                 295                 300

Thr Pro Leu Ile Ser Val Tyr Phe Ala Leu Cys Leu Ser Leu Met Val
305                 310                 315                 320

Val Ser Leu Leu Glu Thr Val Phe Ile Thr Tyr Leu Leu His Val Ala
                325                 330                 335

Thr Thr Gln Pro Pro Met Pro Arg Trp Leu His Ser Leu Leu Leu
            340                 345                 350

His Cys Thr Ser Pro Gly Arg Cys Cys Pro Thr Ala Pro Gln Lys Gly
        355                 360                 365

Asn Lys Gly Leu Gly Leu Thr Leu Thr His Leu Pro Gly Pro Lys Glu
370                 375                 380

Pro Gly Glu Leu Ala Gly Lys Lys Leu Gly Pro Arg Glu Thr Glu Pro
385                 390                 395                 400

Asp Gly Gly Ser Gly Trp Thr Lys Thr Gln Leu Met Glu Leu Trp Val
                405                 410                 415

Gln Phe Ser His Ala Met Asp Thr Leu Leu Phe Arg Leu Tyr Leu Leu
            420                 425                 430

Phe Met Ala Ser Ser Ile Leu Thr Val Ile Val Leu Trp Asn Thr
        435                 440                 445

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: PCR
      distribution oligonucleotide

<400> SEQUENCE: 10
```

```
cgtggaatcc atggatgtgg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: PCR
      distribution  oligonucleotide

<400> SEQUENCE: 11
tggcagggag caagtcattc                                              20

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: PCR
      distribution  oligonucleotide

<400> SEQUENCE: 12
gtgggagatc acagacacgt ctcgcaaagt                                   30
```